(12) United States Patent
Ross et al.

(10) Patent No.: US 11,896,524 B2
(45) Date of Patent: Feb. 13, 2024

(54) TISSUE REMOVAL DEVICES, SYSTEMS AND METHODS

(71) Applicant: Med-Logics, Inc., Athens, TX (US)

(72) Inventors: Rodney L. Ross, Athens, TX (US); James Dennewill, Laguna Hills, CA (US)

(73) Assignee: Med-Logics, Inc., Athens, TX (US)

( * ) Notice: Subject to any disclaimer, the term of this patent is extended or adjusted under 35 U.S.C. 154(b) by 122 days.

(21) Appl. No.: 16/599,887

(22) Filed: Oct. 11, 2019

(65) Prior Publication Data
US 2020/0054487 A1 Feb. 20, 2020

Related U.S. Application Data

(63) Continuation of application No. 14/786,316, filed as application No. PCT/US2014/034606 on Apr. 18, 2014, now Pat. No. 10,441,460, which is a continuation-in-part of application No. PCT/US2013/037478, filed on Apr. 26, 2013.

(51) Int. Cl.
| | | |
|---|---|---|
| *A61F 9/007* | (2006.01) | |
| *A61B 17/00* | (2006.01) | |
| *A61M 1/00* | (2006.01) | |

(52) U.S. Cl.
CPC .......... *A61F 9/00745* (2013.01); *A61F 9/007* (2013.01); *A61F 9/00736* (2013.01); *A61B 2017/00154* (2013.01); *A61B 2017/00176* (2013.01); *A61B 2217/005* (2013.01); *A61M 1/743* (2021.05); *A61M 1/75* (2021.05)

(58) Field of Classification Search
CPC .. A61F 9/00745; A61F 9/007; A61F 9/00736; A61B 2017/00154; A61B 2217/005; A61B 2017/00176; A61M 1/0035; A61M 1/0037
See application file for complete search history.

(56) References Cited

U.S. PATENT DOCUMENTS

| | | | |
|---|---|---|---|
| 3,595,239 A | 7/1971 | Petersen | |
| 3,597,113 A | 8/1971 | Dumoulin et al. | |
| 3,693,613 A | 9/1972 | Kelman | |
| 3,812,855 A * | 5/1974 | Banko | A61M 1/79 137/205 |
| 3,815,604 A | 6/1974 | O et al. | |

(Continued)

FOREIGN PATENT DOCUMENTS

| | | |
|---|---|---|
| CA | 1313802 | 2/1993 |
| CA | 2371812 A1 | 8/2000 |

(Continued)

OTHER PUBLICATIONS

Non final Office Action related to Brazil Application BR112015004855-2 dated Nov. 14, 2019.

(Continued)

*Primary Examiner* — Nilay J Shah
(74) *Attorney, Agent, or Firm* — Olive Law Group, PLLC

(57) ABSTRACT

A tissue removal device includes a hollow needle, an ultrasonic transducer for mechanically vibrating the needle, an aspiration line communicating with the needle, and a vacuum pulsing device for generating vacuum pulses in the needle. The device may be utilized for breaking up tissue by phacoemulsification, vacuum pulsing, or both.

18 Claims, 21 Drawing Sheets

(56) References Cited

U.S. PATENT DOCUMENTS

| | | | |
|---|---|---|---|
| 3,882,872 | A | 5/1975 | Douvas et al. |
| 3,884,238 | A | 5/1975 | O'malley et al. |
| 4,078,564 | A | 3/1978 | Spina et al. |
| 4,135,516 | A | 1/1979 | Spina et al. |
| 4,191,176 | A | 3/1980 | Spina et al. |
| 4,273,261 | A | 6/1981 | Krueger |
| 4,274,411 | A | 6/1981 | Dotson |
| 4,314,560 | A | 2/1982 | Helfgott et al. |
| 4,324,243 | A | 4/1982 | Helfgott et al. |
| 4,591,550 | A | 5/1986 | Hafeman |
| 4,597,388 | A | 7/1986 | Koziol et al. |
| 4,650,470 | A | 3/1987 | Epstein |
| 4,674,499 | A | 6/1987 | Pao |
| 4,744,360 | A | 5/1988 | Bath |
| 4,767,403 | A | 8/1988 | Hodge |
| 4,790,816 | A | 12/1988 | Sundblom et al. |
| 4,925,450 | A | 5/1990 | Imonti et al. |
| 4,933,843 | A | 6/1990 | Scheller et al. |
| 5,022,413 | A | 6/1991 | Spina et al. |
| 5,133,713 | A | 7/1992 | Huang et al. |
| 5,139,504 | A | 8/1992 | Zelman |
| 5,206,255 | A | 4/1993 | Ubasawa et al. |
| 5,217,459 | A | 6/1993 | Kamerling |
| 5,300,069 | A | 4/1994 | Hunsberger et al. |
| 5,312,401 | A | 5/1994 | Newton et al. |
| 5,322,504 | A | 6/1994 | Doherty et al. |
| 5,413,556 | A | 5/1995 | Whittingham |
| 5,417,246 | A | 5/1995 | Perkins et al. |
| 5,423,330 | A | 6/1995 | Lee |
| 5,533,999 | A | 7/1996 | Hood et al. |
| 5,616,120 | A | 4/1997 | Andrew et al. |
| 5,637,112 | A | 6/1997 | Moore et al. |
| 5,651,783 | A | 7/1997 | Reynard |
| 5,674,226 | A | 10/1997 | Doherty et al. |
| 5,674,698 | A | 10/1997 | Zarling |
| 5,691,281 | A | 11/1997 | Ashjian et al. |
| 5,697,281 | A | 12/1997 | Eggers et al. |
| 5,817,050 | A | 10/1998 | Klein |
| 5,885,243 | A | 3/1999 | Capetan et al. |
| 6,017,316 | A | 1/2000 | Ritchart et al. |
| 6,024,731 | A | 2/2000 | Seddon et al. |
| 6,112,123 | A | 8/2000 | Kelleher et al. |
| 6,213,997 | B1 | 4/2001 | Hood et al. |
| 6,228,056 | B1 | 5/2001 | Boehringer et al. |
| 6,268,222 | B1 | 7/2001 | Chandler |
| 6,375,672 | B1 | 4/2002 | Aksan et al. |
| 6,428,508 | B1 | 8/2002 | Ross |
| 6,454,763 | B1 | 9/2002 | Motter et al. |
| 6,468,270 | B1 | 10/2002 | Hovda et al. |
| 6,511,454 | B1 | 1/2003 | Nakao et al. |
| 6,527,766 | B1 | 3/2003 | Bair |
| 6,537,829 | B1 | 3/2003 | Zarling et al. |
| 6,589,237 | B2 | 7/2003 | Woloszko et al. |
| 6,599,271 | B1 | 7/2003 | Easley |
| 6,648,847 | B2 | 11/2003 | Sussman et al. |
| 6,669,685 | B1 | 12/2003 | Rizolu et al. |
| 6,731,963 | B2 | 5/2004 | Finarov et al. |
| 6,884,252 | B1 | 4/2005 | Urich et al. |
| 7,278,836 | B2 | 10/2007 | Hammonds |
| 8,202,287 | B2 | 6/2012 | Staggs |
| 8,617,106 | B2 | 12/2013 | Zacharias |
| 9,188,527 | B2 | 11/2015 | Atzler |
| 9,370,611 | B2 | 6/2016 | Ross et al. |
| 9,561,129 | B2 | 2/2017 | Ross et al. |
| 2001/0034504 | A1 | 10/2001 | Zaleski |
| 2002/0151835 | A1 | 10/2002 | Ross |
| 2003/0144606 | A1 | 7/2003 | Kadziauskas et al. |
| 2003/0158567 | A1 | 8/2003 | Ben-Nun |
| 2003/0228703 | A1 | 12/2003 | Hoppe |
| 2004/0265938 | A1 | 12/2004 | Ramacle |
| 2005/0054971 | A1 | 3/2005 | Steen et al. |
| 2005/0234394 | A1 | 10/2005 | Ross |
| 2005/0234473 | A1 | 10/2005 | Zacharias |
| 2006/0058729 | A1* | 3/2006 | Urich ............... A61M 1/79 604/22 |
| 2006/0293646 | A1 | 12/2006 | Whayne et al. |
| 2007/0016174 | A1 | 1/2007 | Millman et al. |
| 2008/0319374 | A1 | 12/2008 | Zacharias |
| 2009/0142856 | A1 | 6/2009 | Hudack et al. |
| 2010/0010431 | A1 | 1/2010 | Tulley |
| 2010/0035349 | A1 | 2/2010 | Bau et al. |
| 2010/0094199 | A1 | 4/2010 | Steen et al. |
| 2010/0152762 | A1 | 6/2010 | Mark |
| 2010/0184046 | A1 | 7/2010 | Klass |
| 2010/0185150 | A1 | 7/2010 | Zacharias |
| 2010/0191178 | A1* | 7/2010 | Ross ............... A61F 9/00736 604/22 |
| 2010/0280434 | A1 | 11/2010 | Raney et al. |
| 2010/0331764 | A1 | 12/2010 | Boukhny et al. |
| 2011/0178457 | A1 | 7/2011 | Kuebler et al. |
| 2011/0301507 | A1 | 12/2011 | Romano et al. |
| 2012/0089080 | A1 | 4/2012 | Ross et al. |
| 2012/0283575 | A1 | 11/2012 | Rao |
| 2013/0060210 | A1 | 3/2013 | Ross et al. |
| 2013/0150265 | A1 | 6/2013 | Balog et al. |
| 2014/0039111 | A1 | 2/2014 | Winey et al. |

FOREIGN PATENT DOCUMENTS

| | | | | |
|---|---|---|---|---|
| CA | 2690197 | A1 | 12/2008 | |
| CA | 2849419 | A1 | 3/2013 | |
| EP | 1129681 | A1 * | 9/2001 | ......... A61F 9/00745 |
| GB | 2427142 | B | 10/2010 | |
| JP | S59205009 | | 11/1984 | |
| JP | 0234166 | A | 2/1990 | |
| JP | 05047653 | | 6/1993 | |
| JP | 10225476 | A | 8/1998 | |
| JP | 2003534049 | A | 11/2003 | |
| JP | 20050054971 | A | 3/2005 | |
| JP | 2009509632 | A | 3/2009 | |
| JP | 2010531676 | A | 9/2010 | |
| JP | 2012514502 | A | 6/2012 | |
| WO | 0187380 | A1 | 11/2001 | |
| WO | 03043549 | A1 | 5/2003 | |
| WO | 2005097229 | A2 | 10/2005 | |
| WO | 2008157674 | A1 | 12/2008 | |
| WO | 2010054145 | A1 | 5/2010 | |
| WO | 2010080894 | A2 | 7/2010 | |
| WO | 2013039742 | A3 | 5/2013 | |
| WO | 2013184168 | A1 | 12/2013 | |
| WO | 2014039111 | A1 | 3/2014 | |

OTHER PUBLICATIONS

"Tissue Removal Device" Patent Search Report, dated Nov. 6, 2019, Cardinal Intellectual Property.

Non final Office Action regarding related U.S. Appl. No. 13/234,672, dated Feb. 4, 2015.

Non-final Office action dated Jan. 21, 2016 from related U.S. Appl. No. 13/602,925.

Non-Final Office Action from related U.S. Appl. No. 12/683,893, dated Mar. 27, 2012.

Non-Final rejection from related U.S. Appl. No. 12/683,893, dated Dec. 30, 2013.

Non-final rejection from related U.S. Appl. No. 12/683,893, dated Jun. 26, 2014.

Non-final rejection from related U.S. Appl. No. 12/683,893, dated Jun. 24, 2015.

Non-final rejection from related U.S. Appl. No. 12/683,893, dated Mar. 28, 2012.

Non-final Rejection regarding related U.S. Appl. No. 12/683,893 dated Mar. 28, 2012.

Non-Final rejection regarding related U.S. Appl. No. 12/683,893 dated Dec. 30, 2013.

Non-Final rejection regarding related U.S. Appl. No. 12/683,893 dated Jun. 26, 2014.

Non-final rejection regarding related U.S. Appl. No. 12/683,893 dated Jun. 24, 2015.

Office from Canadian Patent Office dated Mar. 27, 2014 for Canadian Application No. 2,750,407.

(56) References Cited

OTHER PUBLICATIONS

Office Action from Canadian Intellectual Property Office (CIPO) regarding related application CA 2910034 dated Feb. 24, 2021 (eight (8) pages).
Advisory action and Examiner initiated interview summary from related U.S. Appl. No. 12/683,893, dated Mar. 3, 2015.
Advisory action and Examiner initiated interview summary regarding related U.S. Appl. No. 12/683,893 dated Mar. 3, 2015.
Amendment from related U.S. Appl. No. 12/683,893 dated Feb. 4, 2015.
Amendment from related U.S. Appl. No. 12/683,893, dated Sep. 23, 2014.
Amendment from related U.S. Appl. No. 12/683,893, dated Mar. 31, 2014.
Amendment regarding related U.S. Appl. No. 12/683,893 dated Aug. 27, 2012.
Amendment regarding related U.S. Appl. No. 12/683,893 dated Mar. 31, 2014.
Amendment regarding related U.S. Appl. No. 12/683,893 dated Sep. 23, 2014.
Amendment regarding related U.S. Appl. No. 12/683,893 dated Feb. 4, 2015.
Amendment regarding related U.S. Appl. No. 12/683,893 dated Dec. 22, 2015.
Applicant initiated interview summary from related U.S. Appl. No. 12/683,893, dated Sep. 9, 2014.
Applicant initiated interview summary from related U.S. Appl. No. 12/683,893, dated Jan. 27, 2015.
Applicant initiated interview summary regarding related U.S. Appl. No. 12/683,893 dated Sep. 9, 2014.
Applicant initiated interview summary regarding related U.S. Appl. No. 12/683,893 dated Jan. 27, 2015.
Australian Examination Report issued in counterpart AU Application No. 2014257365 dated Dec. 19, 2018.
Australian Examination Report issued in counterpart AU Application No. 2014257365 dated Jan. 12, 2018 (three (3) pages.
Australian Notice of Acceptance issued in counterpart AU Application No. 2014257365 dated Jan. 11, 2019.
Brazilian Notice dated Dec. 4, 2018, Journal 2500.
Canadian Examination Report issued in counterpart CA Application No. 2,884,039 dated Feb. 6, 2019.
EP Communication under Rule 71(3) issued in counterpart EP Application No. 13834689.5 dated May 2, 2018 (one-hundred and fourteen (114) pages).
EP Communication under Rule 71(3) issued in counterpart EP Application No. 14787736.9 dated Apr. 30, 2018 (seventy-three (73) pages).
Examination report from related Canadian Patent Application No. 2750407, dated Jan. 8, 2015.
Examination report from related Canadian Patent Application No. 2750407, dated Jun. 5, 2017.
Examination report from related Canadian Patent Application No. 2849419, dated Aug. 2, 2017.
Examination Report No. 1 from related Australian Application No. 2010203588, dated Jan. 4, 2013.
International Search Report and Written Opinion dated Nov. 4, 2010 from related International Application No. PCT/US2010/020348.
Examination report regarding related Canadian Patent Application No. 2750407, dated Mar. 27, 2014.
International Search report from related PCT/US2012/053641, dated Feb. 28, 2013.
Extended European Search Report from related EP Application No. 12830951, dated Apr. 10, 2015.
Extended European Search Report from related EP Application No. 13834689.5 dated Apr. 1, 2016.
Extended European Search Report from related EP Application No. 14787736.9, dated Nov. 25, 2016.
International search report from related PCT/US2013/037478, dated Aug. 21, 2013.
Final rejection from related U.S. Appl. No. 12/683,893, dated Nov. 14, 2014.
Final rejection from related U.S. Appl. No. 12/683,893, dated Sep. 26, 2012.
Final rejection regarding related U.S. Appl. No. 12/683,893 dated Sep. 26, 2012.
Final rejection regarding related U.S. Appl. No. 12/683,893 dated Nov. 14, 2014.
International Preliminary Report and Written Opinion from related PCT/US2014/034606, dated Oct. 27, 2015.
International preliminary report on patentability and written opinion from related PCT/US2010/020348, dated Jul. 12, 2011.
International preliminary report on patentability and written opinion from related PCT/US2012/053641, dated Mar. 18, 2014.
International preliminary report on patentability and written opinion from related PCT/US2013/037478, dated Mar. 10, 2015.
International search report from related PCT/US2014/034606, dated Aug. 25, 2014.
Response to Examination Report and Amendment from related Australian Application No. 2010203588 dated Dec. 17, 2013.
Response and amendment from related Canadian Paten Application No. 2750407, dated Sep. 25, 2014.
RCE and Amendment from related U.S. Appl. No. 12/683,893, dated Mar. 26, 2013.
JP Official action regarding related Japanese Patent Application No. 2011-544687, dated Oct. 16, 2013.
Japanese Office Action issued in counterpart JP Application No. 2016-510708 dated Feb. 20, 2018 with English translation (six (6) pages).
Japanese Office act ion dated Mar. 7, 2017 from related Japanese Application No. JP 2015-529793.
Japanese Notice of Allowance issued in counterpart JP Application No. 2015-529793 dated Jan. 9, 2018 with English translation (four (4) pages).
Japanese-language Office Action issued in counterpart JP Application No. 2016-510708 dated Oct. 23, 2018 (five (5) pages).
Official action from related Japanese Patent Application No. 2011-544687, dated Sep. 25, 2013.
Canadian Examination Report for Corresponding CA Appln No. 2,910,034, dated Feb. 28, 2020.
Office Action dated Oct. 25, 2021 for associated Brazilian Patent Application No. BR112015026633-9 (3 Pages).
Translation of Office Action dated Oct. 25, 2021 for associated Brazilian Patent Application No. BR112015026633-9 (4 Pages).
Response to Office Action dated Jan. 31, 2022 for associated Brazilian Patent Application No. BR112015026633-9 (15 Pages).
Machine Translation of Response to Office Action dated Jan. 31, 2022 for associated Brazilian Patent Application No. BR112015026633-9 (15 Pages).
Notice of Publication dated Nov. 3, 2021 for associated Brazilian Patent Application No. BR112015026633-9 (1 Page).
Office Action dated Mar. 18, 2020 for associated Brazilian Patent Application No. BR112015026633-9 (4 pages).
Machine Translation of Office Action dated Mar. 18, 2020 for associated Brazilian Patent Application No. BR112015026633-9 (4 pages).

\* cited by examiner

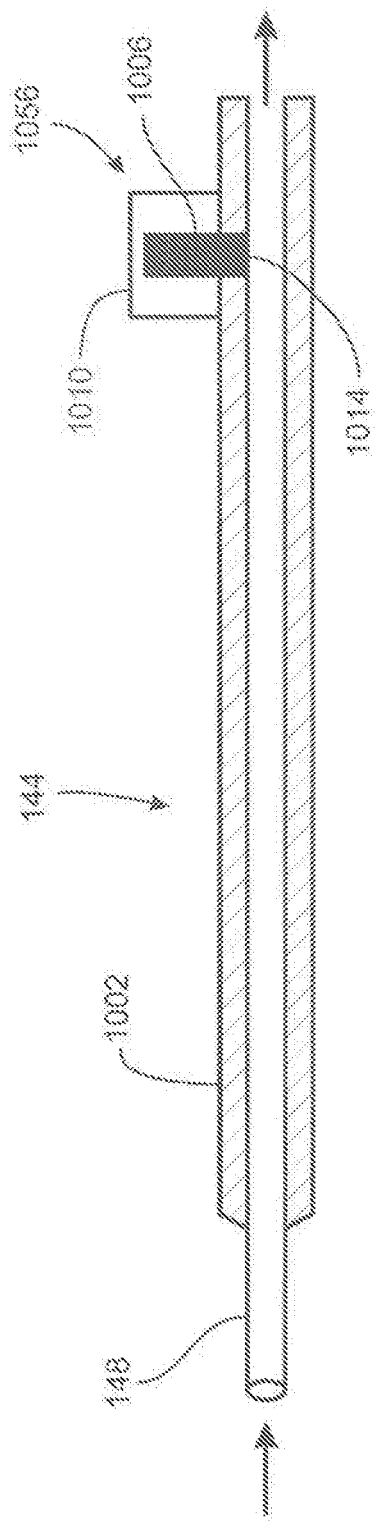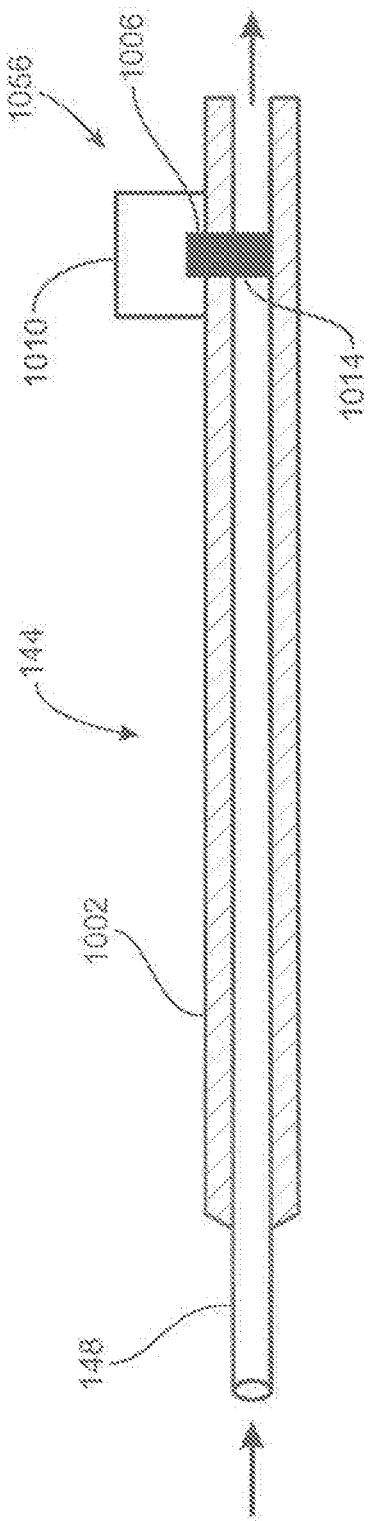

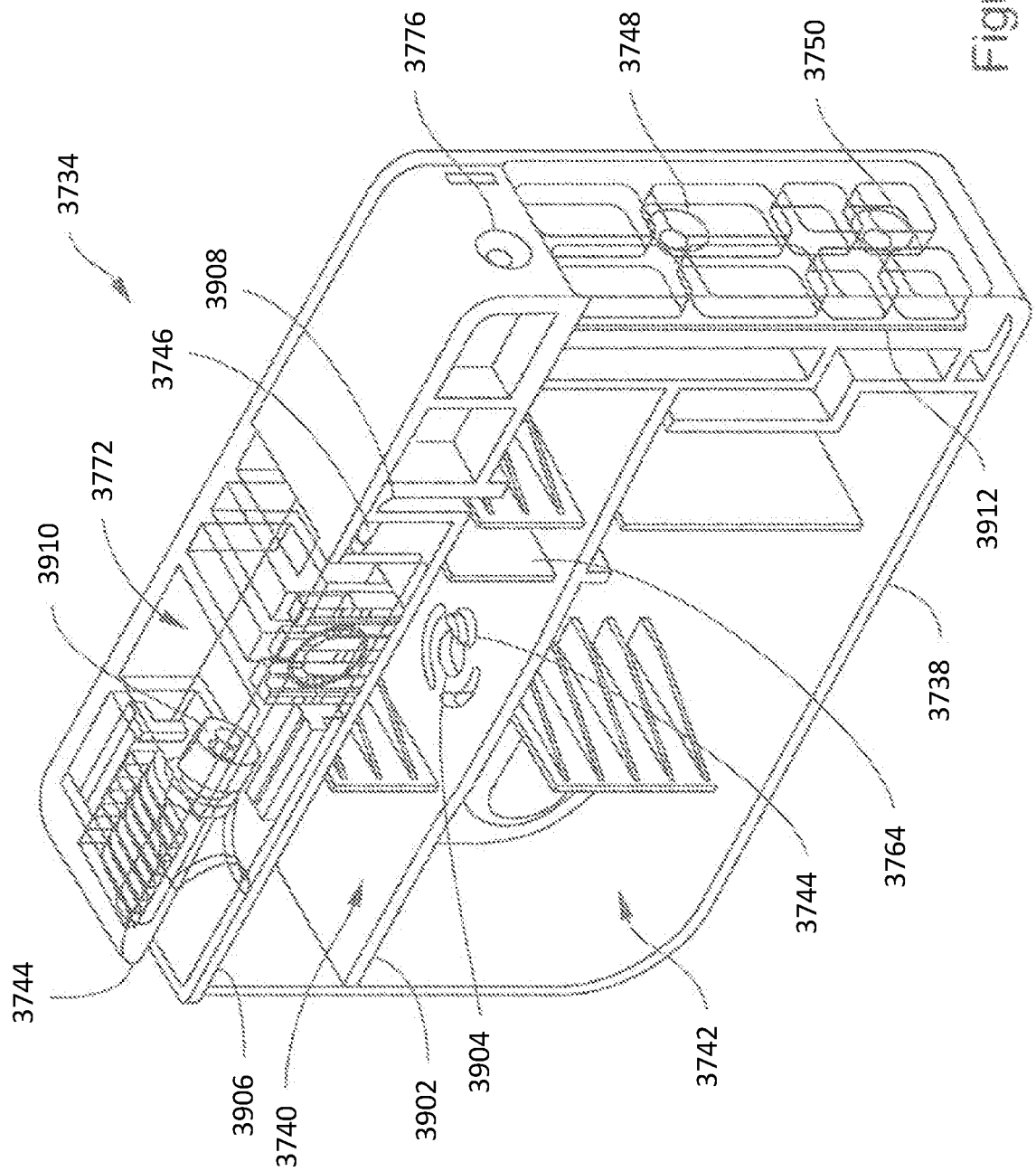

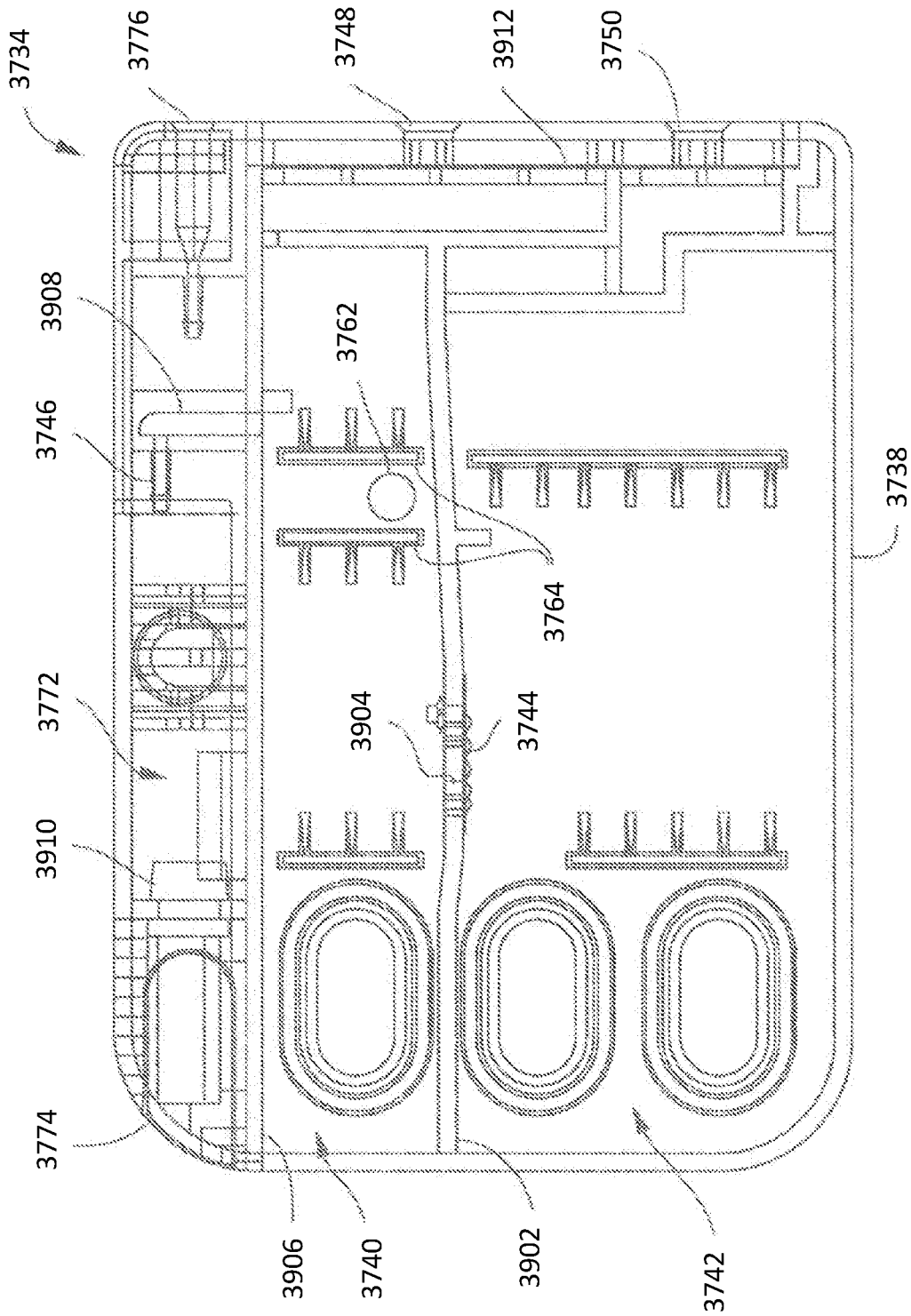

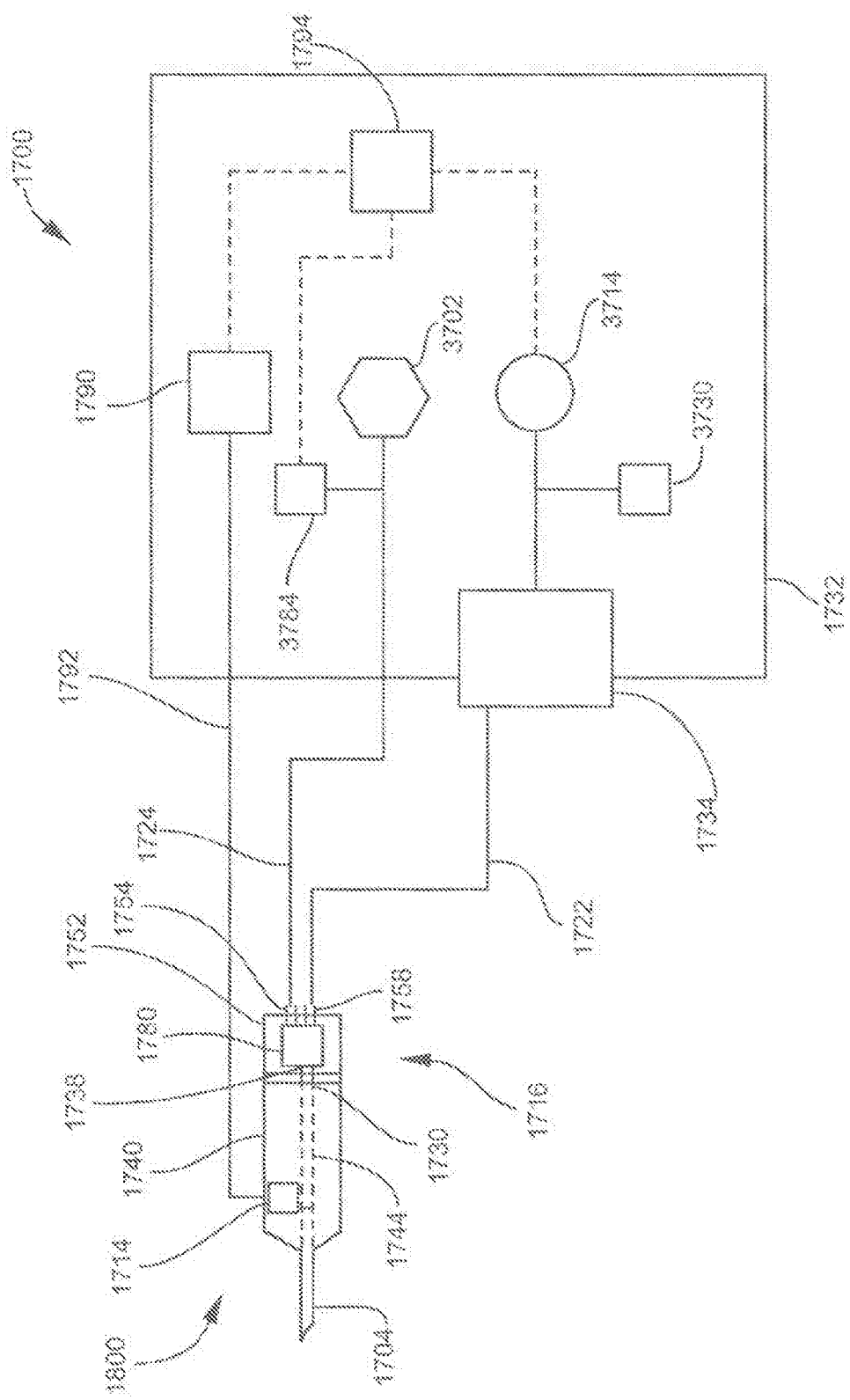

TISSUE REMOVAL DEVICES, SYSTEMS AND METHODS

CROSS REFERENCE TO RELATED APPLICATIONS

This application is related to and claims priority to U.S. Ser. No. 14/786,316 (the entire contents of each of which is incorporated herein by reference). The '316 application is national stage entry of PCT/US2014/034606, filed Apr. 18, 2014, which is a continuation-in-part of and claims priority to PCT/US2013/037478, filed on Apr. 26, 2013, titled "TISSUE REMOVAL DEVICES, SYSTEMS AND METHODS;" which is a continuation-in-part of and claims priority to PCT/US2012/053641, filed on Sep. 4, 2012, titled "TISSUE REMOVAL DEVICES, SYSTEMS AND METHODS;" which is a continuation in part of and claims priority to U.S. application Ser. No. 13/234,672, filed on Sep. 16, 2011, titled "TISSUE REMOVAL DEVICES, SYSTEMS AND METHODS"; which is a continuation-in-part of and claims priority to U.S. application Ser. No. 12/683,893, filed on Jan. 7, 2010, titled "TISSUE REMOVAL DEVICES, SYSTEMS AND METHODS"; which claims priority to U.S. Provisional Patent Application Ser. No. 61/143,010, filed Jan. 7, 2009; the contents of each of which are incorporated by reference herein in their entireties.

TECHNICAL FIELD

The present invention relates generally to the removal of tissue, a non-limiting example of which is the removal of cataract material from the eye of a patient. The invention also relates to selectively utilizing vacuum pulses and/or ultrasonic vibrations to fragment tissue to be removed.

BACKGROUND

Many surgical procedures entail the removal of tissue from the surgical site of operation, including various kinds of ophthalmological procedures. One example of a frequently performed procedure is cataract surgery. The instrument of choice for removing cataracts has been the phacoemulsification ("phaco") device. Phaco technology utilizes ultrasound as the energy modality to fragment and remove the cataract. Specifically, phaco technology uses mechanical ultrasound energy to vibrate a small needle that fragments the cataract material. The needle is typically constructed of titanium, titanium alloy, or surgical-grade steel. During the procedure, aspiration is applied to remove the fragmented cataract material from the eye. Also during the procedure, irrigation fluid (e.g., saline solution) is applied to the eye to help maintain intraocular fluid pressure and neutralize the large amount of heat generated by the vibrating needle. A separate irrigation-aspiration instrument may be utilized, with vacuum applied to a central bore for aspiration and irrigation fluid supplied through an annular passage formed between the central bore and a coaxial sleeve surrounding the central bore. Alternatively, the phaco needle may be hollow to provide the aspiration function, and a separate instrument utilized for irrigation. As a further alternative, the phaco instrument may include a coaxial sleeve surrounding the hollowing needle, or one or more side outlets for irrigation fluid, thus performing both aspiration and irrigation in addition to tissue fragmentation. After the emulsified lens material is removed, it is replaced by an artificial intraocular lens (IOL) as appreciated by persons skilled in the art.

Phaco technology has some disadvantages. The high ultrasonic energy utilized may result in thermal damage to ocular tissue at the incision site. Moreover, the mechanical ultrasound energy delivered through the phaco needle creates a cavitation field that is intended, along with the mechanical movement of the tip, to fragment the cataract material. The cavitation may damage the iris or any ocular tissue or structure exposed to the cavitation. Hence, the surgeon must be very cautious when activating the ultrasound energy inside the eye. The broad propagation of ultrasonic waves and the cavitation are unavoidable consequences of the phaco technique; both are potentially harmful and currently are limitations of conventional phacoemulsification.

Moreover, the ultrasound energy created by the phaco device also is known to damage the endothelial cells, located on the inner lining of the cornea. These cells are critical for quality of vision. The harder the cataract, the greater the endothelial cell loss due to the higher level of ultrasound required to emulsify the cataract. It has been reported that in the use of phaco technology, there is an average endothelial cell loss of 13.74% (1.5 to 46.66%) with cataracts that are from a one-plus to a three-plus hardness. It has also been reported that there is an average endothelial cell loss of 26.06% (6.81 to 58.33%) when removing four-plus hardness cataracts with a phaco device.

Despite the foregoing limitations, phacoemulsification remains an effective technique for breaking up cataract material, particularly cataract material having relatively high hardness (four-plus or higher). There is a need, however, for providing techniques effective for tissue fragmentation and removal based on modalities other than phacoemulsification. There is a need for providing such techniques as alternatives to phacoemulsification or for implementation in combination with phacoemulsification.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a tissue removal device includes: a housing; a hollow needle extending from the housing and comprising an open distal tip outside the housing; an ultrasonic transducer positioned in the housing and configured for mechanically vibrating the needle; an aspiration line communicating with the needle and configured for communicating with a vacuum source outside the housing, wherein the needle and the aspiration line define an aspiration path from the distal tip, through the housing, and out from the housing to the vacuum source, and a vacuum pulsing device positioned outside the housing and configured for generating vacuum pulses at the distal tip, the vacuum pulsing device comprising an actuator and a movable member, wherein the actuator is configured for moving the movable member alternately between a closed position that obstructs the aspiration path and an open position.

According to another implementation, a tissue removal system includes: the tissue removal device; a tissue collection receptacle; and an external aspiration line running from the vacuum pulsing device to the a tissue collection receptacle, wherein the aspiration path runs from the needle, through the housing, through the vacuum pulsing device, through the external aspiration line, and into the tissue collection receptacle.

According to another implementation, a method for removing tissue from a surgical site includes: inserting a distal tip of a hollow needle of a tissue removal device into the surgical site, wherein an ultrasonic transducer of the tissue removal device is coupled to the needle, and the needle is in fluid communication with a vacuum pulsing device; breaking up tissue in the surgical site by operating the tissue removal device according to a mode selected from the group consisting of: a phacoemulsification-only mode in which the ultrasonic transducer vibrates the needle while the vacuum pulsing device is inactive; a vacuum pulsing-only mode in which the ultrasonic transducer is inactive while the vacuum pulsing device applies vacuum pulses to the tissue via the distal tip; and a phacoemulsification-vacuum pulsing mode in which the ultrasonic transducer vibrates the needle and the vacuum pulsing device is active, sequentially or simultaneously with vibrating the needle, to apply vacuum pulses to the tissue via the distal tip; and aspirating the broken up tissue through the needle, through the vacuum pulsing device, and to a tissue collection site.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 4A is a cross-sectional view of an example of a structure of a tissue removal device forming its internal aspiration line, with a vacuum pulsing device in an open position.

FIG. 4B is another cross-sectional view of structure illustrated in FIG. 4A, with the vacuum pulsing device in a closed position.

FIG. 14A is a partially cut-away perspective view of an example of a cassette that may be provided with the tissue removal system illustrated in FIG. 12.

FIG. 14B is a partially cut-away side view of the cassette illustrated in FIG. 14A.

FIG. 17 is a schematic view of an example of a tissue removal device and associated tissue removal system according to another implementation.

DETAILED DESCRIPTION

Figure 1:
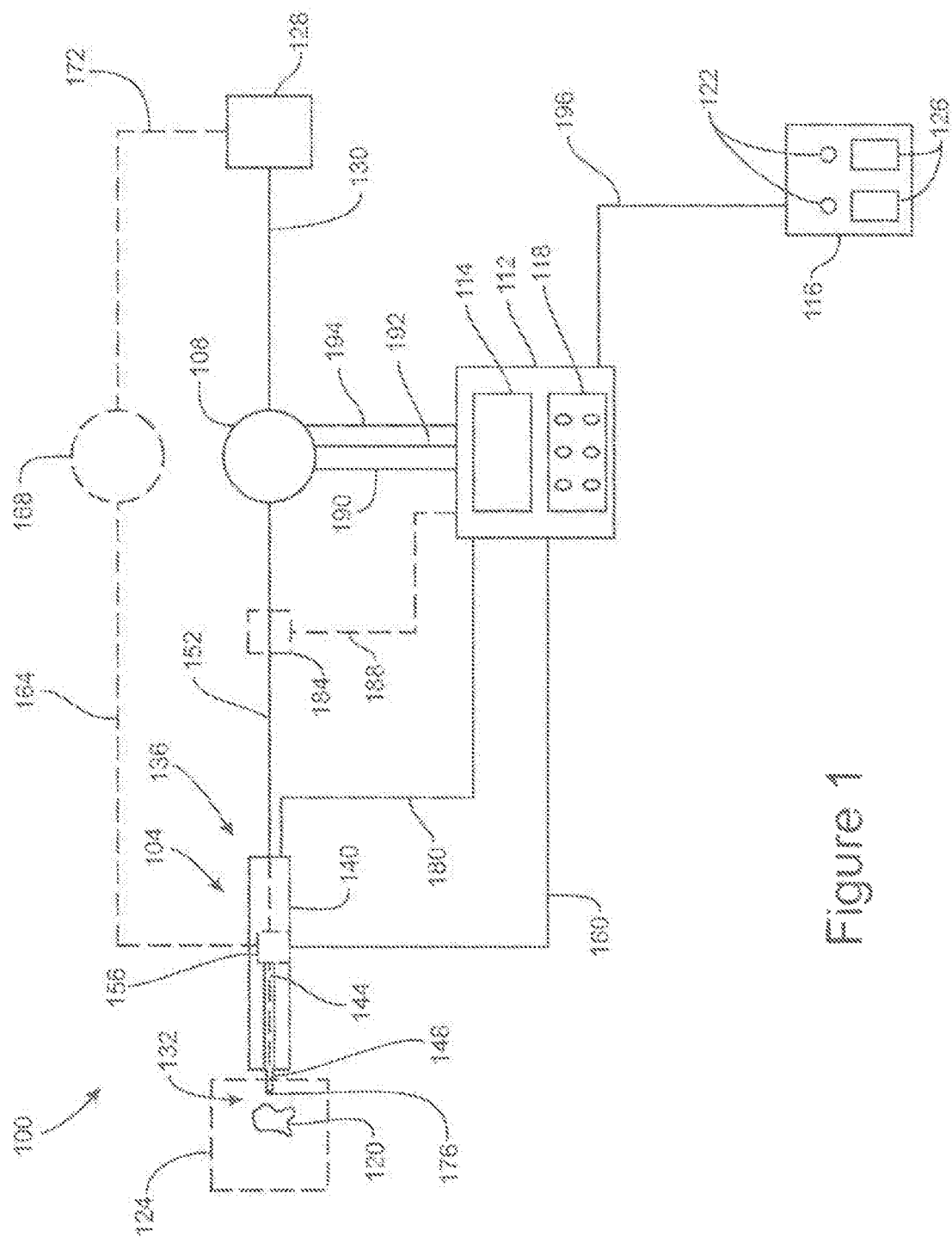
FIG. 1 is a block diagram illustrating an example of a tissue removal system according an implementation of the present invention.

FIG. 1 is a block diagram illustrating an example of a tissue removal system 100 according an implementation disclosed herein. The tissue removal system 100 generally includes a tissue removal device 104, a vacuum pump 108, and one or more system control devices such as a control console 112 and a foot-operated control device 116. In typical implementations, the tissue removal device 104 is structured and sized to be comfortably handheld by a user, and thus may be referred to as a hand piece, a handheld instrument, or a handheld device. Other components of the tissue removal system 100 may be stationary or portable and desired or appropriate for a particular procedure for which the tissue removal system 100 is utilized. The tissue removal device 104 and various other components may be provided to a surgeon in a sterile, preassembled form adapted to be quickly and easily interconnected to complete the tissue removal system 100. The tissue removal device 104 and various other components may be constructed of disposable materials.

Generally, the tissue removal system 100 is adapted for use by a surgeon (or other type of user) to remove target tissue 120 from a surgical site 124 through controlled application of vacuum or both vacuum and ultrasonic energy at a distal tip of the tissue removal device 104. In the present context, target tissue 120 generally encompasses any tissue desired to be removed from the surgical site 124. As an example, the target tissue 120 may be cataract material to be removed from a patient's eye, Vacuum may be utilized not only for aspirating target tissue 120 from the surgical site 124 but also as a modality for breaking up the target tissue 120. Ultrasonic energy may also be utilized for breaking up the target tissue 120. The tissue removal system 100 may also include a tissue collection site 128 such as may be embodied by any suitable receptacle, container or the like, communicating with the vacuum pump 108 via an outlet line 130, for enabling collection and disposal of aspirated tissue in a sterile manner. Depending on the particular application, the tissue removal system may also be configured to add certain types of materials to the surgical site via the tissue removal device 104. For example, the tissue removal system 100 may be adapted to apply irrigation fluid to the surgical site 124, or such function may be performed by a separate instrument. As other examples, the tissue removal device 104 may be configured to inject a material that absorbs cortical material, or a gel or other refractive material that replaces a human lens, a flowable IOL material, etc.

The tissue removal device 104 generally includes an open distal end 132 adapted to be positioned and operated at the surgical site 124, and an opposing proximal end 136. The tissue removal device 104 also includes a housing 140 enclosing various components. As noted above, the housing 140 may be configured (sized, shaped, etc.) to be held in the hand of a surgeon. In advantageous implementations, the housing 140 is constructed of a material that is both electrically and thermally insulating to protect the surgeon, non-limiting examples of which are various thermoplastics and other polymeric compositions. One or more components of the tissue removal device 104 (conduits, tubing, chambers, etc.) provide an internal vacuum (or aspiration) line 144 that runs through the housing 140 generally from the open distal end 132 to or at least toward the proximal end 136. Part of the internal aspiration line 144 is established by a cannula 148 that may extend from a distal opening of the housing 140 over a short distance and terminate at an open distal tip 176 corresponding to the open distal end 132 of the tissue removal device 104. As described below, the cannula 148 may be configured as a phacoemulsification needle (phaco needle). By way of an appropriate fitting (not shown) of the tissue removal device 104 typically located at or near the proximal end 136 (i.e., a proximal opening of the housing 140), the internal aspiration line 144 may be placed in fluid communication with the vacuum pump 108 via connection with an external aspiration line 152 of any suitable length.

The tissue removal device 104 may also include a vacuum pulsing device 156 located within the housing 140 in operative communication with the internal aspiration line 144. With the vacuum pump 108 establishing a controlled level of vacuum, the vacuum pulsing device 156 may be operated to generate vacuum pulses of controlled frequency and duration. For this purpose, the vacuum pulsing device 156 may be placed in electrical communication with the control console 112 via a vacuum pulse control signal line 160. The vacuum pulsing device 156 may be configured in any manner suitable for generating vacuum pulses, some examples of which are described below. To optimize the effect of the vacuum pulsing, the part of the internal aspiration line 144 between the vacuum pulsing device 156 and the open distal end 132 should be rigid so that the as-generated pulsed energy is preserved as it is transferred to the distal end 132. That is, soft conduit materials (e.g., flexible tubing) should be avoided in this part of the internal aspiration line 144 as such materials might provide an undesired damping effect on the pulsed energy. The cannula 148 should thus be constructed from rigid material(s). Depending on the design of the tissue removal device 104, the illustrated cannula 148 may extend from its distal tip 176 to the vacuum pulsing device 156, i.e., over the entire portion of the internal aspiration line 144 that should be rigid. Alternatively, one or more other distinct conduits may be provided between the cannula 148 and the vacuum pulsing device 156, in which case such other conduits should likewise be rigid.

In other embodiments, the vacuum pulsing device 156 may be positioned external to the housing 140. In particular, this may be desired when the tissue removal device 104 is configured for performing phacoemulsification, in which case the vacuum pulsing device 156 may be externally positioned to isolate the vacuum pulsing device 156 from the ultrasonic energy generated in the housing 140.

FIG. 1 also illustrates an additional line 180. Line 180 may schematically represent one or more lines, such as a power line (electrical, pneumatic, etc.) for controlling the vacuum pulsing device 156, an electrical power line for controlling an ultrasonic transducer utilized for phacoemulsification, etc.

In operation, the vacuum pump 108 provides a base level of vacuum for the tissue removal device 104. This vacuum level may be controlled and adjusted as needed by the surgeon for aspirating tissue. Over any given time period during a tissue removal procedure, the surgeon may set the level of vacuum to be constant or may vary the vacuum level. The vacuum pulsing device 156 may be operated to pulse the vacuum generated by the vacuum pump 108. Vacuum pulsing may be performed for any number of purposes, an example of which is to break up target tissue 120 prior to its aspiration. In one particular example, the pulsed vacuum energy is utilized to break up cataract material. The overall duration of the vacuum pulsing (i.e., the time during which the vacuum pulsing device 156 is active), as well as the pulsing parameters (e.g., the magnitude and duration/frequency of the pulses), may be determined by the surgeon. As examples, the surgeon may be allowed to select among various preset (predetermined, preprogrammed, etc.) vacuum pulsing programs, and/or may be allowed to adjust the vacuum pulsing parameters in real time (on the fly). The surgeon may control the operating parameters of the vacuum pump 108 and the vacuum pulsing device 156 by utilizing the control console 112 and/or the foot control device 116.

Figure 2:
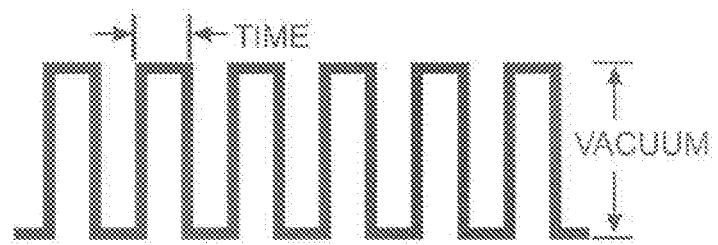
FIG. 2 is an example of a pulsed vacuum signal that may be applied by the tissue removal system.
Figure 3:
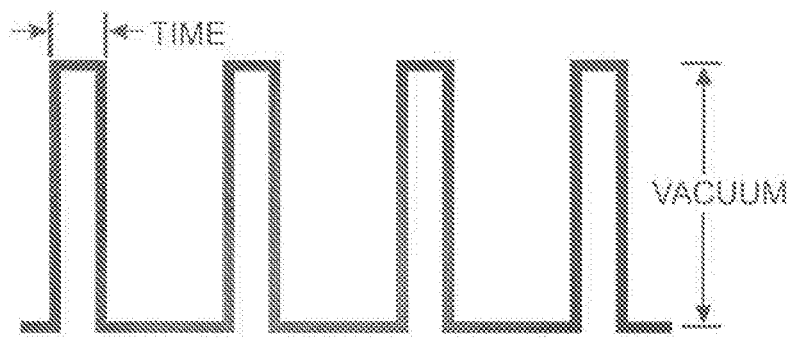
FIG. 3 is another example of a pulsed vacuum signal that may be applied by the tissue removal.

A few examples of vacuum pulsing programs (or profiles) that may be implemented by the vacuum pulsing device 156 are illustrated in FIGS. 2 and 3. Specifically, FIG. 2 is an example of a pulsed vacuum signal characterized by a relatively high-frequency pulse and moderate vacuum level. FIG. 3 is an example of a pulsed vacuum signal characterized by a relatively low-frequency pulse and high vacuum level. In advantageous implementations, the pulse trains have a stepped profile (i.e., are step functions or square waves) as shown in FIGS. 2 and 3, in which the vacuum level abruptly switches between a high value and a low value (which may correspond to zero vacuum or very low vacuum), That is, the transitions between the high and low values are not ameliorated by ramps or curved functions. By this manner, the pulses in effect constitute a sequence of discrete impacts that are effective for breaking up target tissue 120.

For certain specific purposes of vacuum pulsing, such as the breaking up of certain types of tissue, it may be desirable or necessary for the magnitude of the vacuum pulses to be significantly higher than the magnitude of the base vacuum provided by the vacuum pump 108. Hence, the operation of the vacuum pulsing device 156 may be coordinated with the operation of the vacuum pump 108, which may be done automatically by the control console 112. For instance, the control console 112 may be configured to step up the vacuum level generated by the vacuum pump 108 upon activation of the vacuum pulsing device 156, and likewise to step down the vacuum level upon deactivation of the vacuum pulsing device 156. Moreover, as a safety feature, the control console 112 may be configured to shut down the vacuum pump 108 upon deactivation of the vacuum pulsing device 156, or upon sensing a failure of the vacuum pulsing device 156. This type of coordination is particularly useful for certain types of tissue removal procedures such as cataract removal and other ophthalmological procedures. In such operating environments, the higher vacuum level at which the vacuum pulsing operates could, in the absence of the pulsing, create a potentially harmful high fluid flow-rate condition. That is, when the distal tip 176 of the tissue removal device 104 is located in a fluid environment such as the interior of a patient's eye, the vacuum established by operation of the vacuum pump 108 establishes a fluid flow in the direction from the fluid environment toward the vacuum pump 108, through the cannula 148 and all other fluid conduits comprising the aspiration line. When the vacuum pulsing device 156 is not being operated, the flow rate primarily depends on the level of vacuum applied by the vacuum pump 108. The tissue removal system 100 is configured to operate the vacuum pump 108 so as to apply vacuum within a range of magnitudes determined to be effective for aspirating target tissue 120 without damaging or otherwise detrimentally affecting nearby tissue or other structures. On the other hand, when the vacuum pulsing device 156 is also active, the vacuum pulses the cyclical breaking and restoring of the vacuum applied at the distal tip 176 significantly affects the fluid flow rate. Generally, the higher the vacuum pulse rate the lower the fluid flow rate, and the lower the vacuum pulse rate the higher the fluid flow rate. Thus, high-frequency vacuum pulses may be applied at a relatively high magnitude to very effectively break up target tissue 120 in a safe manner because the resultant fluid flow rate remains within a safe range. If, however, the vacuum were to remain at that high magnitude after pulsing ceases due to either deactivation or failure of the vacuum pulsing device 156 then fluid flow rate might quickly increase to an unsafe level. For certain critical surgical sites such as a patient's eye, this sudden jump in fluid flow and/or sudden transition to a continuously applied (non-pulsed) high-magnitude vacuum could cause rapid fluid loss and injury to the patient. Therefore, to eliminate the risk of injury, it is advantageous to coordinate the respective operations of the vacuum pump 108 and the vacuum pulsing device 156.

As just noted, higher vacuum pulse rates result in lower fluid flow rates, and lower vacuum pulse rates result in higher fluid flow rates. Thus, while the tissue removal device 104 is operating in the vacuum-pulse mode the surgeon can control the fluid flow rate, and hence the flow rate of the broken up tissue being aspirated through the tissue removal device 104, by varying the frequency of the vacuum pulses being applied by the vacuum pulsing device 156. The vacuum pulse frequency may be varied by, for example, manipulating an appropriate adjustment knob located on the control console 112 or the foot control device 116. As a safety feature similar to that just described, circuitry provided with the control console 112 or the foot control device 116 may be configured to detect whether a predetermined lower threshold of the vacuum pulse frequency has been reached, and if so respond by automatically lowering the magnitude of the applied vacuum to avoid a dangerously high flow rate. As another safety feature, the foot control device 116 may be configured so as to require a foot switch of the foot control device 116 to remain depressed in order for the vacuum pulsing mode to remain active. By this configuration, if the surgeon intentionally or accidentally removes his foot from the foot switch, the tissue removal system 100 is automatically switched to a continuous vacuum mode with a low vacuum level, or the vacuum pump 108 is automatically shut off, or a valve mechanism of the vacuum pulsing device 156 automatically closes off the aspiration line 144 so as to cut-off application of the vacuum to the distal tip 176 of the cannula 148, etc.

As further shown in FIG. 1, in some implementations the tissue removal system 100 may include a low-vacuum line and a separate high-vacuum line. The above-described first aspiration line 152 is utilized as the low-vacuum line and a second aspiration line 164 is utilized as the high-vacuum line. The first aspiration line 152 and the first vacuum pump 108 are active during the continuous or steady-state vacuum mode in which the surgeon may vary the vacuum level within a range of relatively low vacuum levels. The high-pressure aspiration line 164 interconnects the vacuum pulsing device 156 and a fluid inlet of a second vacuum pump 168 configured for applying relatively higher levels of vacuum associated with the vacuum pulsing mode. Similar to the first vacuum pump 108, the second vacuum pump 168 is controlled by the control console 112 or the foot control device 116 via appropriate electrical signal lines (not shown). The first vacuum pump 108 and the second vacuum pump 168 may be the same type of pump or different types of pumps. The control console 112 or the foot control device 116 is configured to switch between operating the first vacuum pump 108 and the second vacuum pump 168 in accordance with the surgeon's selection of the continuous vacuum mode or the vacuum pulsing mode, or automatically in response to certain events as described elsewhere in the present disclosure. The vacuum pulsing device 156 may be configured to switch the flow path from the cannula 148 into either the first aspiration line 152 or the second aspiration line 164 depending on the mode selected. Thus, fluid and removed tissues flow through either the first aspiration line 152 or the second aspiration line 164. An outlet line 172 may interconnect a fluid outlet of the second vacuum pump 168 and the tissue collection site 128.

The tissue removal device 104 may be utilized in a variety of procedures that entail inserting the cannula 148 into a surgical site via an incision. For instance, in various ophthalmological procedures, an incision may be made through a membrane of a patient's eye. The incision may be made by various techniques such as, for example, a laser procedure. To minimize damage to the eye and minimize post-surgery recovery and healing periods, the incision should be as small as possible. Therefore, the cannula 148 should be as small as practicably possible. The design of the cannula 148 disclosed herein enables its size to be minimized without adversely affecting its function. In some implementations, the outer diameter of the cannula 148 ranges from about 1.0-3.0 mm. In some examples, the outer diameter of the cannula 148 is about 3.0 mm, 2.5 mm, 2.0 mm, 1.5 mm, or 1.0 mm. The size of the cannula 148 is able to be minimized in part because the tissue removal device 104 itself is not required to provide a means for supplying irrigation fluid to the surgical site 124. The utilization of the vacuum pulsing effect disclosed herein does not require nearly as much irrigation fluid as tissue removal techniques of the prior art. Any irrigation fluid needed to be added to the surgical site 124 may be supplied by a separate hand-held device. This may be referred to as a bimanual technique in which the surgeon wields the tissue removal device 104 in one hand and an irrigating device in the other hand as needed. Alternatively, the tissue removal device 104 may be configured for performing a coaxial technique in which irrigation fluid is supplied by the tissue removal device 104 through an annular sleeve (not shown) coaxial with the cannula 148. This latter alternative would require a larger incision, although the incision may still be less than 3.0 mm.

Additionally, the tissue removal system 100 may be configured to detect the occurrence of occlusion and automatically activate one or more different modes of operation. Various approaches may be taken for detecting the occluding event. As one non-limiting example, the tissue removal system 100 may provide a pressure transducer 184 (FIG. 1), operatively interfaced with the aspiration line 152 at an appropriate location thereof, which provides continuous or intermittent pressure feedback signals to the control console 112 via a pressure feedback signal line 188. The detection of an abrupt change in pressure (or vacuum) level in the aspiration line 152 may be interpreted as the occurrence of an occluding event at the distal tip 176 and automatically trigger a different mode of operation. When the tissue removal system 100 is operating in continuous vacuum mode, the detection of an occluding event may automatically trigger activation of the vacuum pulsing mode. The control console 112 may be configured to decide whether to automatically trigger the vacuum pulsing mode and/or any other mode disclosed herein, and whether to activate two or more modes simultaneously or sequentially, depending on the current state of operation of the tissue removal device 104 at the time of detection of an occlusion. When it is subsequently detected that the occlusion has been lost, the control console 112 may be configured to deactivate the vacuum pulsing device 156, and/or may shut down the vacuum pump(s) 108, 168 or otherwise cause vacuum to be cut off at the distal tip 176. For the purpose of detecting occlusions, the pressure transducer 184 may be positioned in the housing 140 (FIG. 1) of the tissue removal device 104 in operative communication with some portion of the internal aspiration line 144. Alternatively, as shown in FIG. 1 the pressure transducer 184 may be positioned in operative communication with the external aspiration line 152 or 164, or within the housing of the vacuum pump 108 or 168.

While the various cannulas 148 described thus far are oriented along a straight axis, this is not a limitation of the present teachings. In some implementations, the cannula 148 provided with the tissue removal device 104 may be curved or angled. In other implementations, the radius of curvature or the angle of the cannula 148 may be adjustable. That is, the surgeon may elect to utilize a straight-shaped cannula 148 or be able to bend the cannula 148 to conform to a desired curved or angled shape. This adjustability of the cannula 148 may be implemented in a variety of ways, such as by selecting a material that is malleable (yet still rigid so as not to dampen vacuum pulses), providing the cannula 148 in the form of a series of segments that are movable relative to each other, etc. An adjustable cannula 148 may be useful in certain surgical sites that are difficult to access, do not have straight boundaries, or have unpredictable boundaries. A few examples include blood vessels, various biological ducts, and various anatomical cavities.

FIGS. 4A and 49 are cross-sectional views of an example of a structure of the tissue removal device 104 forming its internal aspiration line 144. FIG. 4A shows the aspiration line 144 in an open position, while FIG. 4B shows the aspiration line 144 in a closed position. The structure includes the cannula 148, another suitable fluid conduit such as a tube 1002 in fluid communication with the cannula 148, and a vacuum pulsing device 1056 in operative communication with the aspiration tube 1002. The cannula 148 may be structured according to any of the implementations described herein. As noted above, the cannula 148 and at least that portion of the aspiration tube 1002 between the vacuum pulsing device 1056 and the cannula 148 should be rigid so as to optimize the vacuum pulsing effect. The vacuum pulsing device 1056 may have any design suitable for alternately closing and opening the fluid path through the aspiration tube 1002 and hence alternately breaking and restoring vacuum. For this purpose, in some implementations the vacuum pulsing device 1056 includes a movable member 1006 that may be actuated by an actuator 1010 to alternately extend into and retract from the fluid path. The movable member 1006 may be configured to obstruct all or part of the fluid path when extended therein such that the cycling of the movable member 1006 between its extended and retracted positions generates vacuum pulses. As noted above, the vacuum pulsing effect may be utilized to break up target tissue. The vacuum pulsing effect may be implemented alternatively or in conjunction with phacoemulsification. Moreover, the vacuum pulsing effect and phacoemulsification may be implemented in sequence or simultaneously. When implemented in sequence, the vacuum pulsing effect may follow phacoemulsification, or vice versa. The sequencing of the two effects may be repeated over one or more alternating cycles. Accordingly, in a given tissue removal procedure, a surgeon may elect to activate the vacuum pulsing effect only, or phacoemulsification only, or both effects according to a desired sequence, or both effects simultaneously to achieve a synergistic effect.

In some embodiments, the vacuum pulsing device 1056 is a solenoid-based device in which case the actuator 1010 is a solenoid actuator. The movable member 1006 serves as the plunger that is translated by the actuator 1010. The movable member 1006 translates through an opening 1014 in the aspiration tube 1002. A seal of any suitable design may be provided at the physical interface between the movable member 1006 and the tube opening 1014 as needed to maintain the aspiration tube 1002 in a fluid-tight condition. As one non-limiting example, the seal may be an elastic material that covers the tube opening 1014. As the movable member 1006 translates into the aspiration tube 1002 through the tube opening 1014, the seal stretches and deforms around the movable member 1006, thereby coveting the movable member 1006 as well as the tube opening 1014 and maintaining fluid isolation between the interior and exterior of the aspiration tube 1002.

Figure 5A:
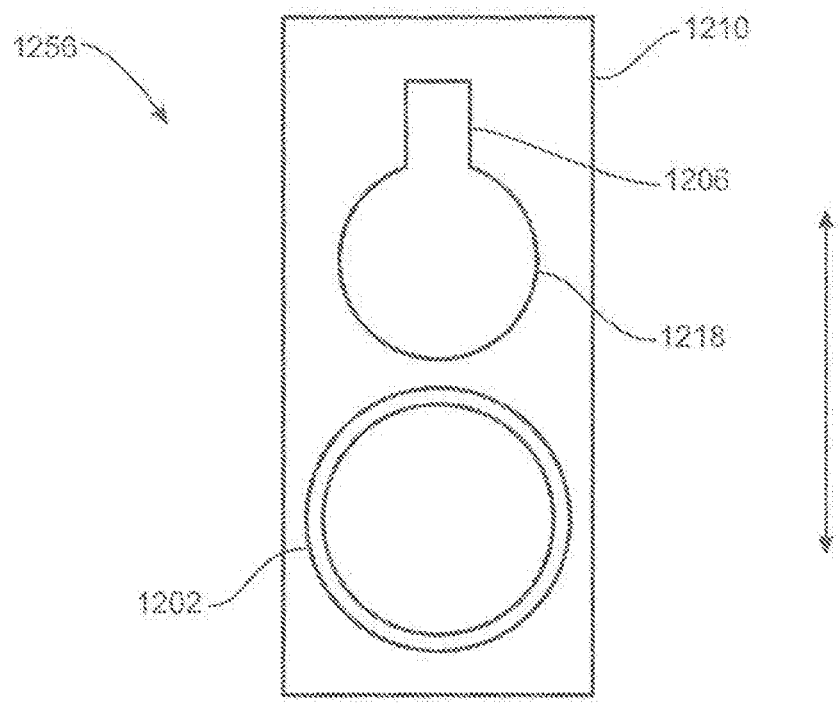
FIG. 5A is a cross-sectional view of another example of a vacuum pulsing device with a movable member thereof in a retracted position.
Figure 5B:
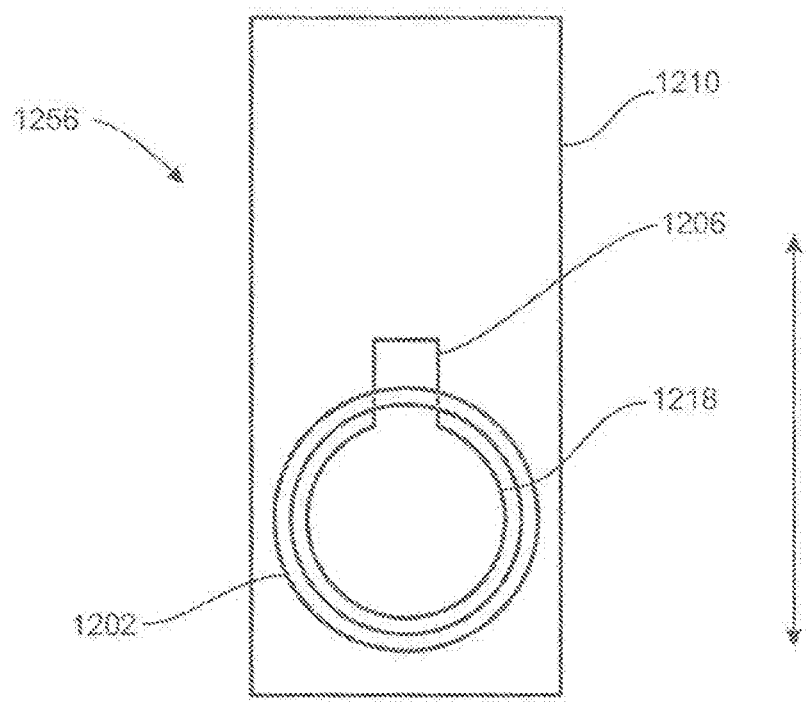
FIG. 5B is a cross-sectional view of the vacuum pulsing device illustrated in FIG. 5A, with the movable member in its extended position.

FIGS. 5A and 5B are cross-sectional views of another example of a solenoid-based vacuum pulsing device 1256. The vacuum pulsing device 1256 includes a solenoid actuator 1210 and a movable member 1206 reciprocated by the actuator 1210 into and out from the flow path of an aspiration tube 1202 of the tissue removal device 104. FIG. 5A illustrates the movable member 1206 in its retracted position and FIG. 5B illustrates the movable member 1206 in its extended position. In this example, the movable member 1206 includes a distal section 1218 having a cross-sectional area substantially equal to the cross-sectional area of the aspiration tube 1202. By this configuration, the vacuum pulsing device 1256 effects complete or nearly complete occlusion of the flow path through the aspiration tube 1202 when the movable member 1206 is in the fully extended position.

Figure 6:
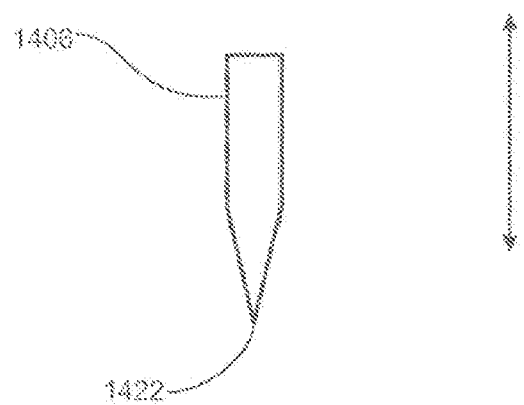
FIG. 6 is a side elevation view of an example of a movable member that may be provided in a vacuum pulsing device.

FIG. 6 is a side elevation view of a movable member 1406 from a perspective transverse to the direction of fluid flow in an aspiration tube. The movable member 1406 may be provided in a solenoid-based vacuum pulsing device such as described above in conjunction with FIGS. 4A and 4B or FIGS. 5A and 5B. In this example, the movable member 1406 tapers down to a sharp edge 1422. By this configuration, the movable member 1406 may be utilized to further break up any tissue flowing through the aspiration tube while the movable member 1406 is being cycled into the aspiration tube.

Figure 7A:
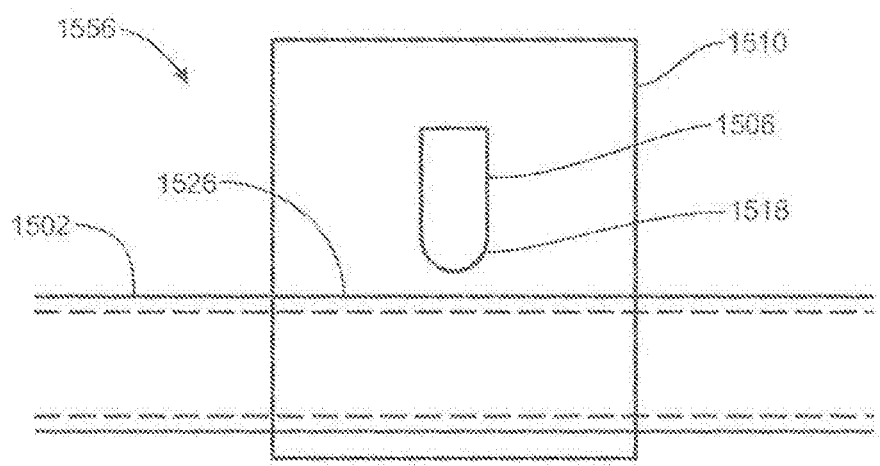
FIG. 7A is a cross-sectional view of another example of a vacuum pulsing device with a movable member thereof in a retracted position.
Figure 7B:
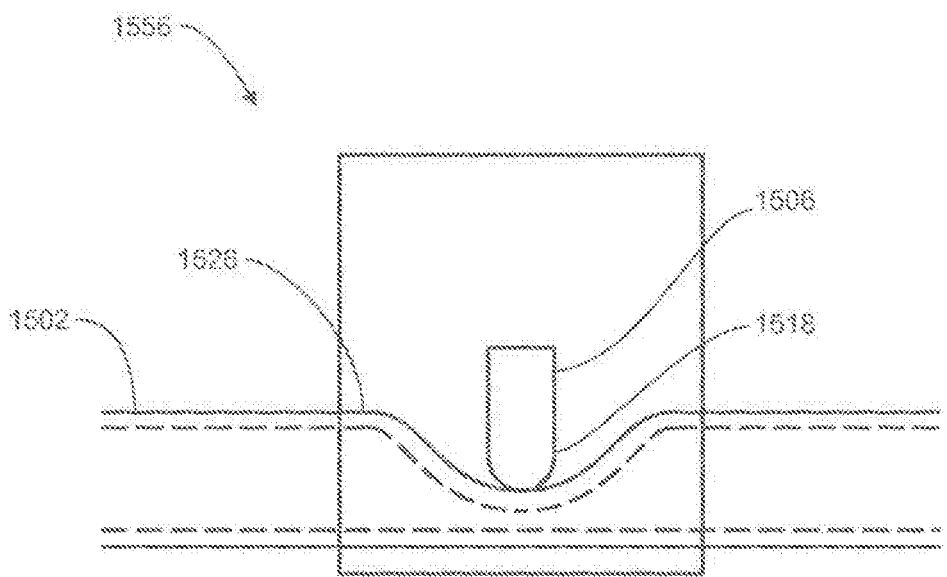
FIG. 7B is a cross-sectional view of the vacuum pulsing device illustrated in FIG. 7A, with the movable member in its extended position.

FIGS. 7A and 7B are cross-sectional views of another example of a solenoid-based vacuum pulsing device 1556. The vacuum pulsing device 1556 includes a solenoid actuator 1510 and a movable member 1506 reciprocated by the actuator 1510 toward and away from the flow path of an aspiration tube 1502 of the tissue removal device 104. FIG. 7A illustrates the movable member 1506 in its retracted position and FIG. 7B illustrates the movable member 1506 in its extended position. In this example, the vacuum pulsing device 1556 is designed as a pinch valve. The movable member 1506 includes a distal section 1518 having a rounded end. A section 1526 of the aspiration tube 1502 immediately underneath the movable member 1506 is constructed from a deformable material (e.g., flexible tubing). As the movable member 1506 is translated to its fully extended position, the movable member 1506 comes into contact with the outside surface of the flexible section 1526 and deforms the flexible section 1526 until opposing regions of the inner wall of the flexible section 1526 come into contact with each other, thereby pinching off the flow path through the aspiration tube 1502.

Referring back to FIG. 1, the vacuum pump 108 generally includes a housing, a fluid inlet, a fluid outlet, and vacuum-generating components (not shown). The fluid inlet may be placed in fluid communication with the tissue removal device 104 via the (first) external aspiration line 152. The fluid outlet may be placed in fluid communication with the tissue collection site 128 via the outlet line 130. The external aspiration lines 152, 130, 164, 172 may have any suitable fluid-conducting structure (e.g., tubing), may be of any suitable length, and may be either rigid or flexible. The vacuum pump 108 may be any suitable pump for generating a controlled level of vacuum at the distal end 132 of the tissue removal device 104. The magnitude (or level) of vacuum may be set high enough to enable target tissue 120 to be aspirated through the cannula 148, the internal aspiration line 144, the first external aspiration line 152, the vacuum pump 108, the outlet line 130, and to the tissue collection site 128.

In some implementations, the vacuum pump 108 has a dual-cylinder configuration in which a pair of motorized syringe-type pumping units is disposed in, the housing. In this case, the vacuum generating components may include a pair of cylinders, a pair of pistons reciprocating in the respective cylinders, and a pair of motors controlling the reciprocal movement of the respective pistons. The internal passages of the vacuum pump 108 may include a pair of inlet passages interconnecting the first aspiration line 152 and the respective cylinders, and a pair of outlet passages interconnecting the respective cylinders and the outlet line 130. Actively controlled valves may be provided in each inlet passage and outlet passage. The pistons are reciprocated at or about 180 degrees out-of-phase with each other. Accordingly, while one piston is executing a suction stroke the other piston is executing a discharge stroke. Consequently, while fluid from the first aspiration line 152 is being drawn into one cylinder, fluid previously drawn into the other cylinder is being discharged into the outlet line 130. In addition, a pair of pressure transducers may be disposed in fluid communication with the respective cylinders to measure the vacuum in each cylinder. An example of this type of dual-cylinder pump is described in U.S. Patent Application Pub. No. 2005/0234394, which is incorporated by reference herein in its entirety.

Continuing with this example, the motors of the vacuum pump 108 are in signal communication with the control console 112 via a motor control signal line 190. The valves are in signal communication with the control console 112 via a valve control signal line 192. The pressure transducers are in signal communication with the control console 112 via a pressure feedback signal line 194. By this configuration, the control console 112 is able to monitor and adjust the respective speeds of the pistons and their relative positions (i.e., relative timing or phasing), switch the positions of the valves between ON and OFF positions and possibly intermediate positions between the ON and OFF positions, and monitor the vacuum levels in each cylinder so as to make control decisions based on measured vacuum levels. By this configuration, the control console 112 is able to synchronize the respective operations of the motors and valves to maintain a constant vacuum level in the aspiration line 152. The vacuum level may be selected by the surgeon by manipulating controls on the control console 112 or the foot control device 116. This configuration also enables the vacuum pump 108 to respond quickly to real-time adjustments to the vacuum level made by the surgeon while minimizing transitory instabilities in the vacuum level caused by changing the vacuum level.

As diagrammatically illustrated in FIG. 1, the control console 112 may include a display 114 for outputting information to the surgeon. The control console 112 may also include a variety of controls or input mechanisms 118 (switches, knobs, keypad, etc.) for enabling the surgeon to input information, set and adjust various operating parameters of the tissue removal system 100 (e.g., vacuum pump(s) 108 and 168, vacuum pulsing device 156, phacoemulsification-related parameters such as on/off and sonic/ultrasonic frequency, etc.), and program or adjust the control mechanisms provided by the foot control device 116. The control console 112 also includes electronic hardware (circuitry) and memory for storing software. The circuitry includes interface circuitry for enabling the respective operations of the display 114 and the input mechanisms 118, and for interfacing with the foot control device 116. The circuitry and software are configured for supporting the various functions of the tissue removal system 100. As examples, the circuitry may be configured for monitoring the operations of the vacuum pump(s) 108 and 168, the vacuum pulsing device 156, and an ultrasonic transducer utilized for phacoemulsification, and for sending appropriate control signals to these components. Software may be provided for programming the circuitry for controlling these components in a manner appropriate for the particular tissue removal procedure to be performed. In some implementations, one or both vacuum pump(s) 108 and 168 may be mounted at or within the control console 112. In other implementations, one or both vacuum pump(s) 108 and 168 may be mounted at or within the foot control device 116.

By utilizing the input mechanisms of the control console 112 the surgeon may, as examples, switch the vacuum pump(s) 108 and 168 ON or OFF, set and vary the vacuum level generated by the vacuum pump(s) 108 and 168, switch the vacuum pulsing device 156 ON or OFF, set and vary the pulse frequency of the vacuum pulsing device 156 (thereby also controlling the flow rate of aspirated tissue), set and vary the magnitude of the vacuum pulses, switch the ultrasonic excitation ON or OFF, set and vary the frequency of the ultrasonic excitation, etc. The control console 112 may also be configured to enable the surgeon to switch between a mode in which the surgeon can control the vacuum pulse rate and vacuum pulse magnitude together as a single operating parameter by making a single adjustment, and a mode in which the surgeon can control the vacuum pulses rate and vacuum pulse magnitude independently by manipulating two separate input mechanisms. Similarly, the control console 112 may be configured to enable the surgeon to switch between a mode in which the surgeon can control one or more operating parameters of phacoemulsification together with one or more parameters of the vacuum pulsing device 156, and a mode in which the surgeon can control the operating parameters of phacoemulsification independently of the operating parameters of the vacuum pulsing device 156.

The control console 112 may also be configured to enable the surgeon to switch the vacuum pulsing device 156 to a single-pulse mode that activates the vacuum pulsing device 156 only momentarily so as to apply a single pulse at a predetermined vacuum pulse magnitude. The single-pulse mode may be useful, for example, in an ophthalmological procedure that calls for creating an entry into the anterior capsule of a patient's eye. In this example, prior to breaking up target tissue, the distal tip 176 of the cannula 148 may be placed into contact with the exterior of the anterior capsule. During this time, the tissue removal device 104 may be operated in the continuous-vacuum mode to assist in bringing the distal tip 176 into contact with anterior capsule. The vacuum pulsing device 156 is then switched to the single-pulse mode, whereby the impact imparted by the single pulse is sufficient to create an entry into the anterior capsule through the thickness of its exterior structure. The distal tip 176 is then inserted through the entry, at which time a tissue removal procedure may be performed. This technique enables the creation of an entry having a size and shape precisely conforming to the size and shape of the cannula 148, thereby providing a superior seal between the anterior capsule and the cannula 148.

The foot control device 116 may be configured for controlling one or more of the same functions controllable by the control console 112, such as those just described. Accordingly, the foot control device 116 may include one or more input mechanisms such as adjustable knobs 122 and depressible foot pedals 126. The foot pedals 126 may include foot switches and/or pivoting foot pedals. Foot switches may be operated to switch components of the tissue removal system 100 between ON and OFF states, or for clicking through incremental adjustments to operating parameters (e.g., selecting a high, medium or low setting for the applied vacuum or electrical energy). Pivoting foot pedals may be utilized to vary operating parameters between minimum and maximum values. The adjustable knobs 122 on the foot control device 116 or those on the control console 112 may be configured to enable the surgeon to set the minimum and maximum values of the pivoting foot pedal, and/or the rate (e.g., linear or exponential) by which an operating parameter changes in response to the pivoting travel of the foot pedal. As an example, pivoting the foot pedal forward from its base position to its halfway position may cause the associated operating parameter to be adjusted to a value that is exactly 50% of the preset maximum value. As another example, pivoting the foot pedal forward from its base position to its halfway position may result in adjusting the associated operating parameter to a value that is 75% of its preset maximum value, in which case adjusting the operating parameter over the other 25% up to the maximum value would require pivoting the foot pedal forward from the halfway position through the remaining portion of the pedal's travel. The control console 112 and/or the foot control device 116 may be configured to enable the surgeon to select which functions or operations are to be controlled by the control console 112 and which functions or operations are to be controlled by the foot control device 116. For simplicity, the foot control device 116 is diagrammatically illustrated in FIG. 1 as communicating with the control console 112 over a wired or wireless communication link 196. It will be understood, however, that depending on the functions controllable by the foot control device 116, various electrical signal lines may run directly to the foot control device 116 as an alternative or additionally to those communicating with the control console 112.

Figure 8:
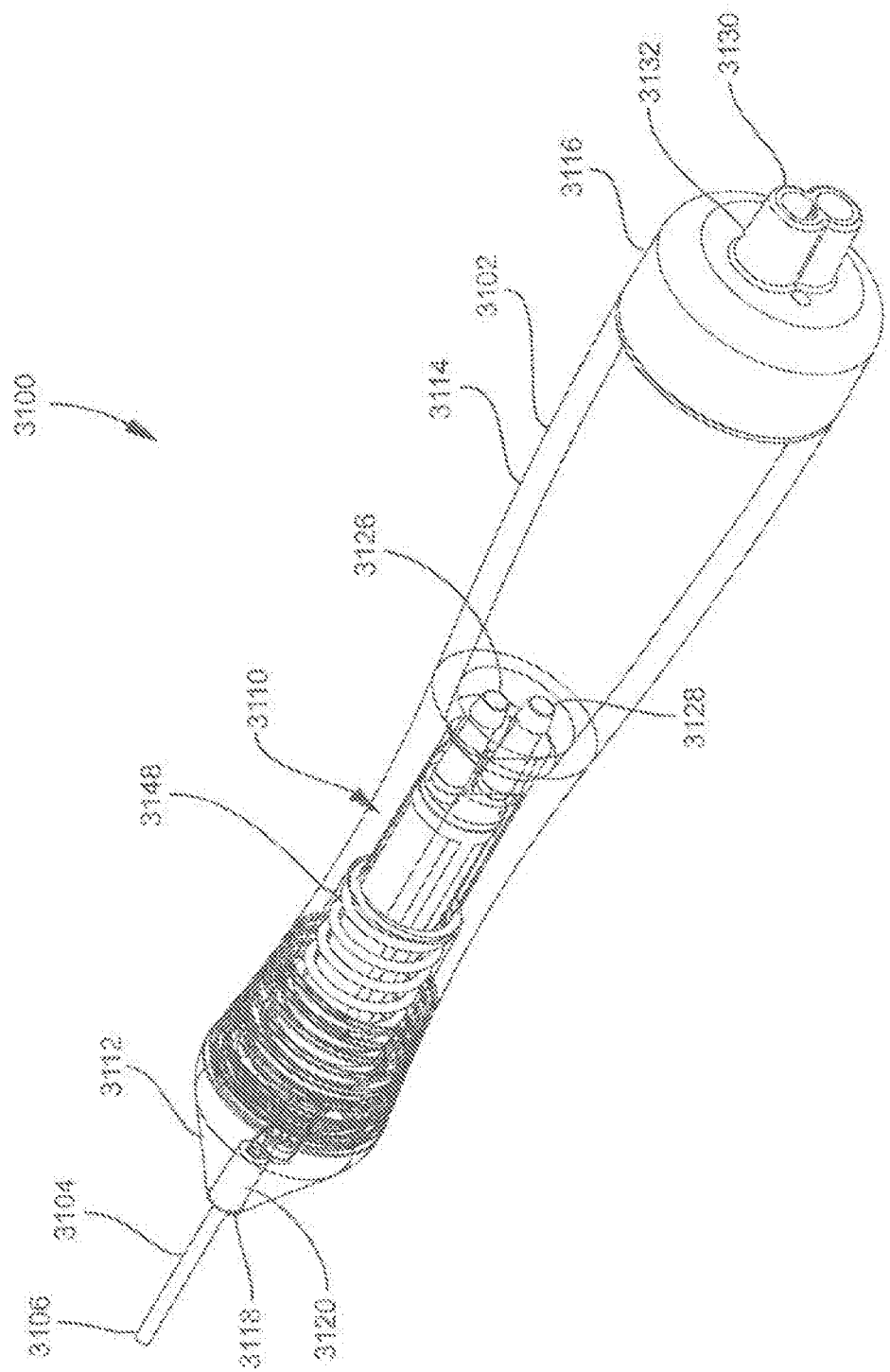
FIG. 8 is a perspective view of an example of a tissue removal device according to another implementation.
Figure 9:
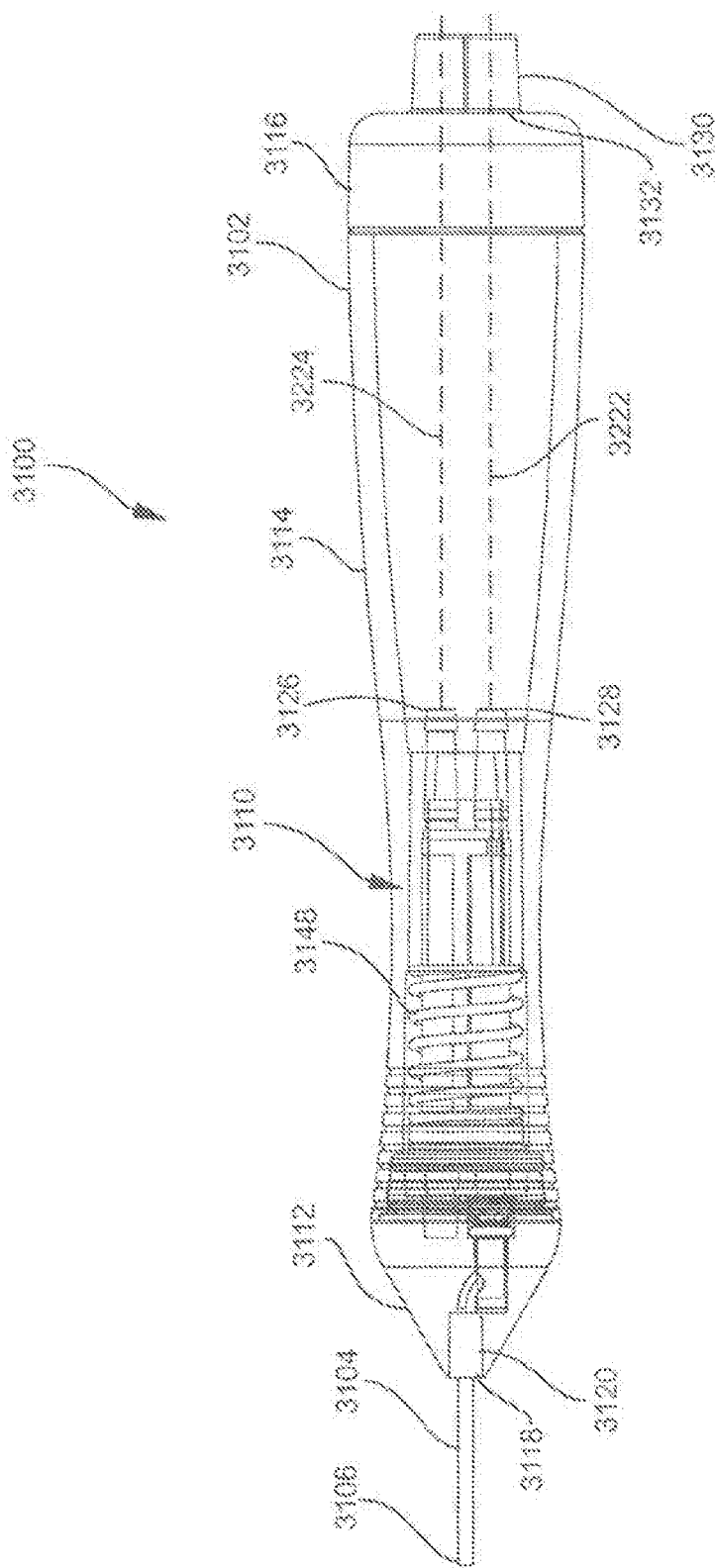
FIG. 9 is a plan view of the tissue removal device illustrated in FIG. 8.

FIGS. 8 and 9 are perspective and plan views, respectively, of an example of a tissue removal device 3100 according to another implementation. The tissue removal device 3100 is generally configured as a handpiece, or hand-held instrument, sized and shaped to be held by a user. The tissue removal device 3100 includes handpiece housing 3102 that encloses various components in its interior, an aspiration cannula 3104 of rigid composition extending from the interior to a distal tip 3106 outside the housing 3102, and a valve assembly 3110 disposed in the interior. The housing 3102 may generally be elongated along a longitudinal axis of the tissue removal device 3100. The housing 3102 may include a plurality of sections assembled together. In the illustrated example, the housing 3102 includes a distal (or front) body 3112 from which the aspiration cannula 3104 extends, a main (or intermediate) body 3114 coupled to the distal body 3112 in a fluid-sealed manner and elongated along the longitudinal axis, and a proximal (or rear) body 3116 coupled to the main body 3114 opposite to the distal body 3112. In the present context, the term "fluid-sealed" means "gas-tight" or "vacuum-tight" and refers to a sealed condition that eliminates or at least substantially minimizes the transfer of gas across or through the interface or component being as described as "fluid-sealed." The distal body 3112 includes a distal housing opening 3118 through which the aspiration cannula 3104 extends in a fluid-sealed manner. For this purpose, a distal seal 3120 of suitable configuration and composition may be provided at the interface between the aspiration cannula 3104 and the distal housing opening 3118.

In some implementations, the tissue removal device 3100 is designed to be disposable, in which case the tissue removal device 3100 is provided to the user in a permanent form. In the present context, the term "permanent" (e.g., permanently assembled, installed, coupled, etc.) means that the tissue removal device 3100 is not able to be disassembled by a user without damaging the tissue removal device 3100 or rendering it inoperable. For instance, the various sections of the housing 3102 are not able to be disassembled, the aspiration cannula 3104 is not able to be removed from the housing 3102, and the fluid lines are not able to be removed from the housing 3102.

In the illustrated example, the valve assembly 3110 is pneumatically-actuated and is configured for applying vacuum to, and inducing controlled vacuum pulses in, the aspiration cannula 3104. For this purpose, the valve assembly 3110 communicates with the aspiration cannula 3104, and with an aspiration line 3222 and a pressurized gas line 3224 that are depicted as dashed lines in FIG. 9. The aspiration line 3222 and pressurized gas line 3224 may be flexible tubes that extend out from the housing 3102 via feed-through members. The valve assembly 3110 may include a gas line fitting 3126 and an aspiration line fitting 3128 configured for attachment to the tubes. In the illustrated example, a single feed-through member 3130 having two bores extends through a proximal housing opening 3132 of the proximal body 3116. A gap between the bores accommodates a dual-lumen construction in which the respective tubes for the aspiration line 3222 and pressurized gas line 3224 are integrally connected side-by-side by an intervening strip of material (not shown). In the illustrated example, the tubes are flexible to accommodate reciprocating action of the valve assembly 3110, as described below. In other implementations, the aspiration line 3222 and pressurized gas line 3224 may pass through the housing 3102 via a side opening or openings thereof, and/or may pass through housing 3102 via separate openings.

Figure 10:
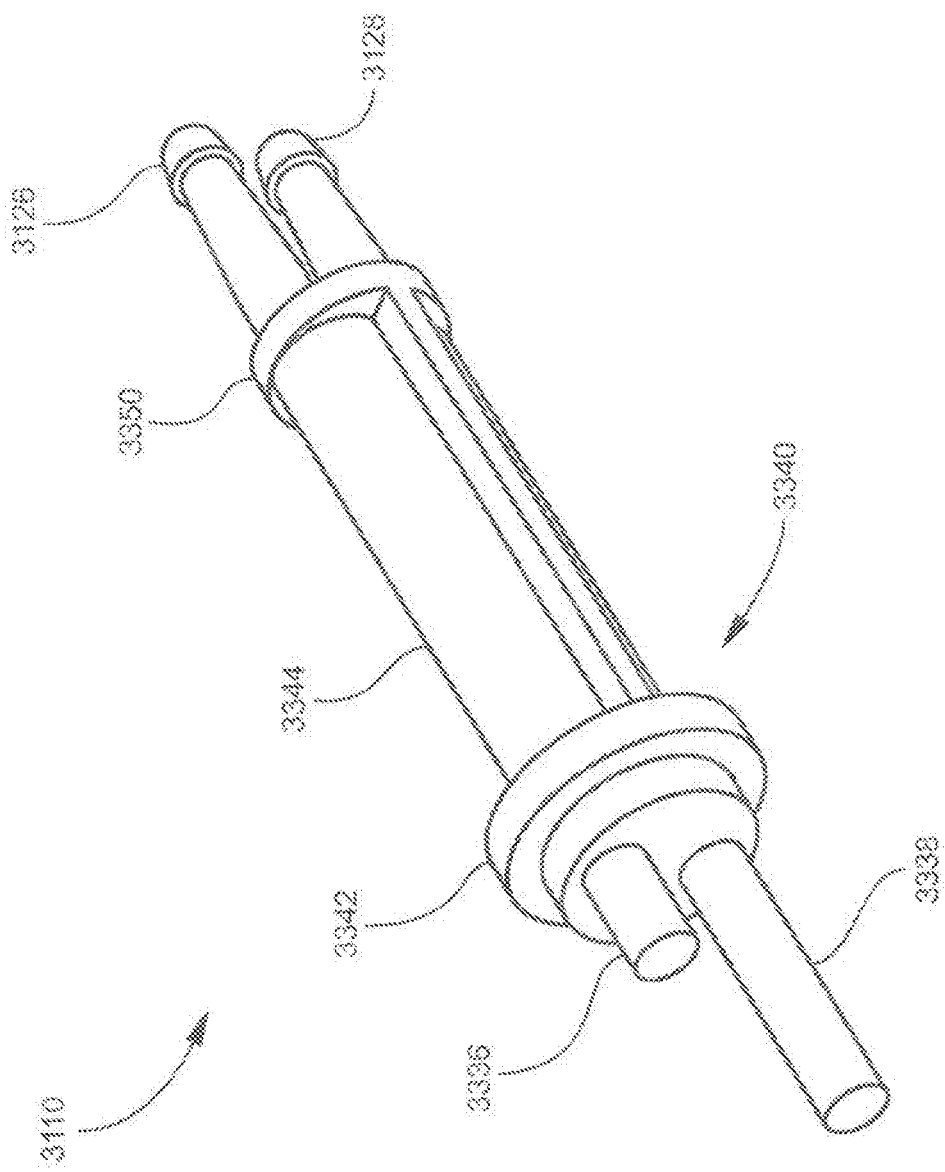
FIG. 10 is a perspective view of an example of a valve assembly that may be provided with the tissue removal device illustrated in FIGS. 8 and 9.

FIG. 10 is a perspective view of an example of the valve assembly 3110. The valve assembly 3110 includes a gas conduit (or gas cannula) 3336, an inner cannula 3338, and a piston 3340. The gas conduit 3336, inner cannula 3338 and piston 3340 may be constructed of rigid materials such as various metals and polymers. The piston 3340 may include a piston head (or flange) 3342 and a sleeve 3344 coaxially surrounding the gas conduit 3336 and inner cannula 3338. The piston 3340 (e.g., the piston head 3342 or an end portion of the sleeve 3344) may include bores through which the gas conduit 3336 and inner cannula 3338 extend. As described further below, the valve assembly 3110 is configured to be pneumatically actuated between an open position and a closed position. In the open position, the valve assembly 3110 completes an aspiration path from the aspiration cannula 3104, through the inner cannula 3338 and out from the housing 3102 to enable aspirant (e.g., tissue and fluid) to be aspirated to a collection receptacle, in the closed position, the valve assembly 3110 blocks the aspiration path. The valve assembly 3110 may be reciprocated between the open and closed positions according to a desired pulse profile such as illustrated, for example, in FIGS. 2 and 3, to control fluid flow and break up tissue as described earlier in the present disclosure. In the present implementation, the valve assembly 3110 is configured to be normally biased into the closed position b spring force and positively actuated into the open position by application of gas pressure against the spring force. That is, the forward stroke of the valve assembly 3110 (toward the closed position) is spring-actuated and the rearward stroke (toward the open position) is pneumatically actuated. For this purpose, the valve assembly 3110 includes a spring 3148 (FIGS. 8 and 9) mounted in the housing 3102 between the piston head 3342 and an internal wall of the housing 3102 and coaxially surrounding the sleeve 3344. The piston head 3342 thus has an outer diameter larger than that of the sleeve 3344 such that the piston head 3342 contacts the spring 3148. A proximal portion 3350 of the sleeve 3344 may be configured to come into abutment with a suitable stop member, such as an internal wall (not shown) of the housing 3102, to provide a limit on the maximum rearward stroke of the valve assembly 3110. The proximal portion 3350 may be provided with a resilient member (not shown) to facilitate contact with the stop member.

In the present implementation, the valve assembly 3110 is spring-biased into the closed position as a safety measure to prevent vacuum from being applied to a surgical site such as a patient's eye at undesired times. In another implementation, the components of the valve assembly 3110 may be configured such that the valve assembly 3110 is spring-biased into the open position and pneumatically actuated into the closed position. In another implementation, the valve assembly 3110 may be configured for being pneumatically actuated into both the open position and closed position.

Figure 11A:
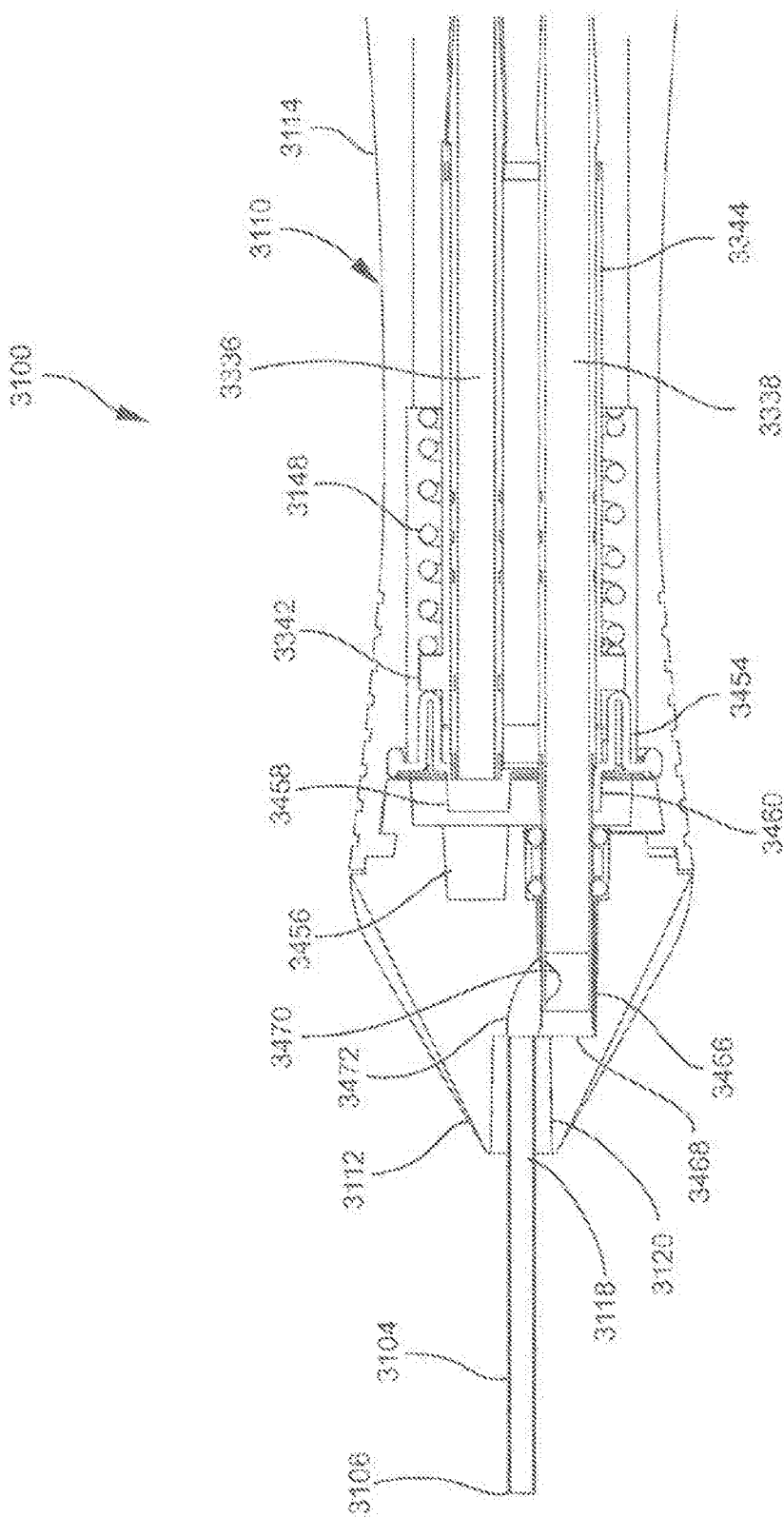
FIG. 11A is a cross-sectional view of the tissue removal device illustrated in FIGS. 8 and 9, with the valve assembly in the open position.

FIG. 11A is a cross-sectional view of the tissue removal device 3100 with the valve assembly 3110 in the open position. The distal body 3112 may be secured to the main body 3114 of the housing 3102 by any suitable fluid-sealing means, which may include the use of one or more o-rings or other types of sealing elements. In implementations where the tissue removal device 3100 is disposable, the distal body 3112 may be secured to the main body 3114 in a permanent manner. In the present implementation, the linear actuator includes a diaphragm 3454 securely mounted transversely to the longitudinal axis and coaxially surrounding the gas conduit 3336 and inner cannula 3338. The diaphragm 3454 may be composed of any suitable flexible material capable of withstanding repeated cycling of gas pressurization and forcible contact with the piston head 3342. Additionally, one or more inside walls or surfaces of the housing 3102 define a gas chamber 3456 on the distal side of the diaphragm 3454. These inside walls or surfaces may be part of the distal body 3112, the main body 3114, or both. The gas chamber 3456 is bounded on at least one side by the diaphragm 3454, whereby the diaphragm 3454 provides a fluid-sealed boundary between the gas chamber 3456 and the other portion of the interior of the housing 3102. The volume of the gas chamber 3456 varies in accordance with the degree to which the diaphragm 3454 is expanded or contracted in response to gas pressure within the gas chamber 3456.

In some implementations, the diaphragm 3454 includes a first bore 3458 through which the gas conduit 3336 passes and a second bore 3460 through which the inner cannula 3338 passes. The diaphragm material is tightly compressed around the gas conduit 3336 at the first bore 3458 and around the inner cannula 3338 at the second bore 3460. The gas conduit 3336 passes through the first bore 3458 into the gas chamber 3456, such that an open distal end of the gas conduit 3336 communicates with the gas chamber 3456. The distal end of the gas conduit 3336 translates back and forth within the gas chamber 3456 as the valve assembly 3110 reciprocates through the forward and rearward strokes. The gas chamber 3456 is shaped to accommodate this translation.

In the illustrated example, the inner cannula 3338 passes through the second bore 3460, through the gas chamber 3456, and into an outer cannula 3466 disposed in the distal body 3112. The distal body 3112 and outer cannula 3466 may be fluidly isolated from the gas chamber 3456 by any suitable manner. In the illustrated example, the interface between the inner cannula 3338 and the opening in the gas chamber 3456 leading into the distal body 3112 is sealed by a seal interposed between the gas chamber 3456 and the outer cannula 3466. In the illustrated example, the seal includes a pair of o-rings separated by an annular spacer. The outer cannula 3466 includes a distal end that is closed off in a secure, fluid-sealed manner by a resilient seal 3468 (e.g., a plug, stopper, closure, etc.). The outer cannula 3466 also includes a valve port 3470 that communicates with the aspiration cannula 3104. The inner cannula 3338 and outer cannula 3466 thus form a linearly actuated valve that communicates with the aspiration cannula 3104 in a fluid-sealed manner.

The valve port 3470 may be formed through the cylindrical wall of the outer cannula 3466. In some implementations, the valve port 3470 is a side port oriented ninety degrees to the aspiration cannula axis. In the present context, the term "ninety degrees" is not limited to exactly ninety degrees, and thus encompasses the terms "substantially ninety degrees" and "about ninety degrees." The valve port 3470 may communicate with the aspiration cannula 3104 via a transition 3472 disposed between, and fluidly communicating with, the aspiration cannula 3104 and the valve port 3470. The transition 3472 may be an angled section (e.g., a bent section, curved section, elbow section, etc.). In some implementations, depending on construction, the transition 3472 may be considered to be integrally part of, or an extension of, a distal section of the aspiration cannula 3104 that extends along an aspiration cannula axis in a straight manner. In other implementations, the transition 3472 may be considered to be a separate component disposed between the aspiration cannula 3104 and the outer cannula 3466. The transition 3472 is "angled" relative to the aspiration cannula axis—that is, the transition 3472 follows a curved or bent path from the aspiration cannula 3104 to the valve port 3470. Although the valve port 3470 is oriented 90 degrees to the aspiration cannula axis, in some implementations it is preferred that the transition 3472 terminate with a profile by which the transition 3472 transitions to the valve port 3470 at an angle less than 90 degrees. This configuration is illustrated by a dotted line in FIG. 11A, and may provide a smoother (less abrupt) aspiration pathway from the aspiration cannula 3104 into the inner cannula 3338. The transition 3472 is adjoined (e.g., welded, bonded, etc.) to the surface of the outer cannula 3466 surrounding the valve port 3470 in a fluid-sealed manner. If the transition 3472 is a separate component from the aspiration cannula 3104, the transition 3472 is likewise adjoined to the aspiration cannula 3104 in a fluid-sealed manner.

In the present implementation, the aspiration cannula 3104, transition 3472, outer cannula 3466 and inner cannula 3338 are all composed of a rigid material, such as a metal or rigid polymer. By this configuration, the entire aspiration path from the distal tip 3106 of the aspiration cannula 3104 to the valve assembly 3110 is defined by rigid structures, which facilitates the application of very precise and controlled vacuum pulses in accordance with the present teachings. In some implementations, the inside diameter of the valve port 3470 is equal to or greater than the inside diameter of the distal tip 3106. In some implementations, the inside diameter of the valve port 3470 is larger than the inside diameter of the distal tip 3106, which facilitates an expanding cross-sectional flow area of the aspiration path and prevents clogging of tissue in the aspiration path. The inside diameter of the transition 3472 may gradually increase from that of the aspiration cannula 3104 to that of the valve port 3470. In some implementations, the inside diameter of the distal tip 3106 ranges from 0.2 mm to 2 mm, and the inside diameter of the valve port 3470 ranges from 0.05 mm to 5 mm.

In operation, the rearward stroke of the valve assembly 3110 into the open position shown in FIG. 11A is effected by flowing pressurized gas from a suitable pressurized gas source (not shown) through the gas line 3224 (FIG. 9), through the gas conduit 3336, and into the gas chamber 3456. As gas pressure increases in the gas chamber 3456, it forces the diaphragm 3454 to expand in the rearward direction. The diaphragm 3454 is either already in contact with the piston head 3342 or expands into contact with the piston head 3342. In either case, the expanding diaphragm 3454 forces the piston head 3342 in the rearward direction against the biasing force imparted by the spring 3148. During expansion of the diaphragm 3454, the piston head 3342 is either already in contact with the spring 3148 or comes into contact with the spring 3148 as a result of the expansion. In the present implementation, as shown in FIG. 11A, the entire valve assembly 3110 is translated in the rearward direction with the piston head 3342. In particular, the inner cannula 3338 is translated rearward through the stationary outer cannula 3466. Due to the rearward translation, an open distal end of the inner cannula 3338 clears the valve port 3470. Hence, an open aspiration path is established, which runs from the distal tip 3106, and through the aspiration cannula 3104, the transition 3472, the valve port 3470, the open space in the outer cannula 3466 between the resilient seal 3468 and the open distal end of the inner cannula 3338, the inner cannula 3338, the remaining portion of the aspiration line 3222 (FIG. 9), and to a collection receptacle (not shown) external to the tissue removal device 3100.

Figure 11B:
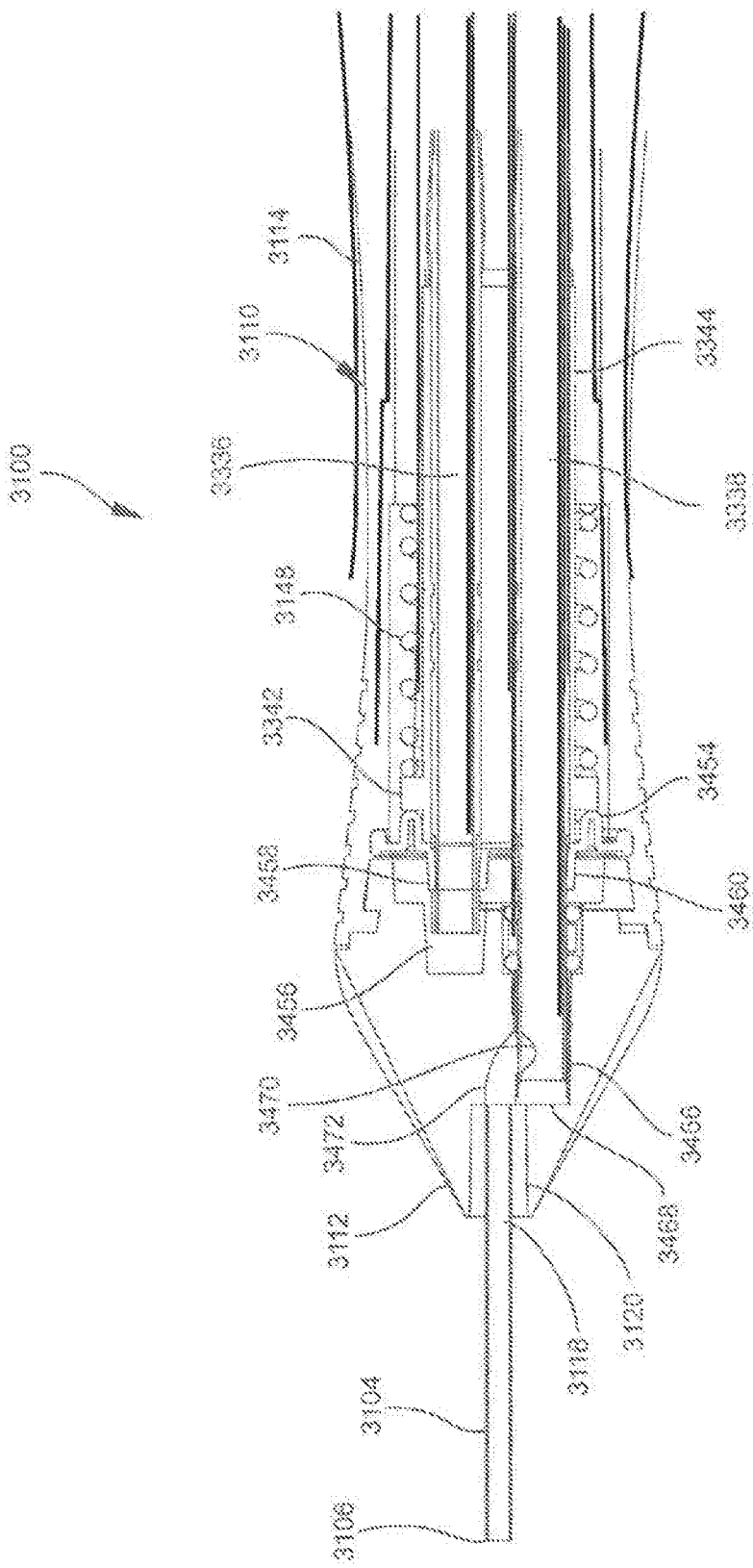
FIG. 11B is a cross-sectional view of the tissue removal device illustrated in FIGS. 8 and 9, with the valve assembly in the closed position.

FIG. 11B is a cross-sectional view of the tissue removal device 3100 with the valve assembly 3110 in the closed position. The closed position is attained by ceasing the flow of pressurized gas into the gas chamber 3456, or reducing the flow enough to enable the diaphragm 3454 to contract and the valve assembly 3110 to translate in the forward direction back to the closed position, which is assisted by the spring 3148. In the closed position, the inner cannula 3338 is translated forwardly through the outer cannula 3466 and comes into fluid-sealed contact with the resilient seal 3468. In this position, the inner cannula 3338 completely blocks (or occludes) the valve port 3470, thereby breaking the application of vacuum in the aspiration cannula 3104.

It can be seen that through appropriate control of the pressurized gas flow to the valve assembly, the valve assembly 3110 may be reciprocated back and forth between the open and closed positions at any desired frequency to achieve a desired vacuum-pulsing effect. The level of vacuum applied to the aspiration cannula 3104, the activation of vacuum pulsing, and adjustment of the pulsing parameters may be controlled by a user via a control console and/or a foot pedal, as described earlier in this disclosure.

It can be seen that in the implementation illustrated in FIGS. 8 to 11B, the tissue removal device 3100 includes an internal valve that is reciprocated between open and closed positions by a pneumatically-driven linear actuator. A feature of the internal valve is the valve port 3470 (defined in the illustrated example by the stationary outer cannula 3466) with which the aspiration cannula 3104 is in fluid communication. The valve port 3470 is alternately opened and closed by linear movement of the inner cannula 3338, which in the illustrated example not only serves as a valve component but also as part of the aspiration line through the handheld instrument. By this configuration, the axis of the aspiration cannula 3104 is offset from the axis of the inner cannula 3338, the aspiration cannula 3104 and the inner cannula 3338 may be parallel or substantially parallel, and the valve port 3470 is oriented transversely or substantially transversely to the aspiration cannula 3104 and the inner cannula 3338. This configuration enables the internal valve to be reliably actuated between open and closed positions in a very vacuum-tight manner over a wide range of frequencies, thereby enabling precise, robust control over vacuum pulsing.

It will be understood that the tissue removal device 3100 illustrated in FIGS. 8 to 11B is but one implementation, and that other implementations are encompassed by the presently disclosed subject matter. As examples, the gas chamber 3456 and diaphragm 3454 may be configured such that the inner cannula 3338 does not pass through them, and such that the inner cannula 3338 and/or other components of the internal valve are fluidly isolated from the gas chamber 3456 without the use of specific sealing elements. The valve assembly 3110 and diaphragm 3454 may be configured such that the gas conduit 3336 and inner cannula 3338 do not pass through the diaphragm 3454. The valve assembly 3110 may be configured such that the gas conduit 3336 does not pass through the piston 3340 and/or the gas conduit 3336 is stationary. The valve assembly 3110 may be configured such that the inner cannula 3338 is mechanically linked to the piston 3340 but does not pass through the piston 3340. Moreover, in other implementations, the linear actuator may utilize a pneumatically-driven component other than a flexible diaphragm. In still other implementations, the operation of the linear actuator may be based on non-pneumatic means, such as mechanical, electrical, electromechanical, or electromagnetic means. In further embodiments, the actuator may be a rotary actuator instead of a linear actuator.

Figure 12:
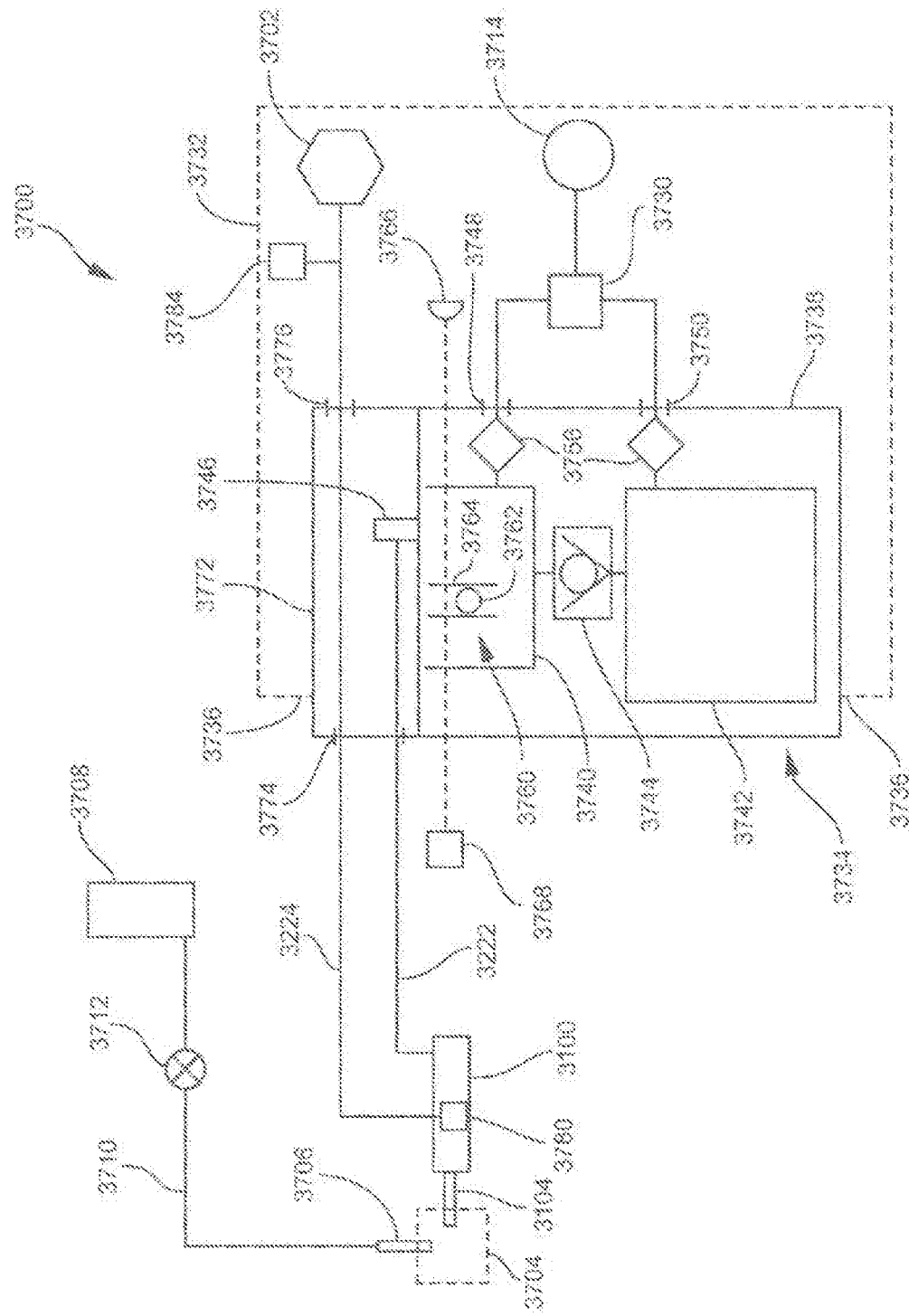
FIG. 12 is a schematic view of an example of a tissue removal system according to another implementation.

FIG. 12 is a schematic view of an example of a tissue removal system 3700 according to another implementation. The tissue removal system 3700 includes a tissue removal device and a tissue (and fluid) collection receptacle communicating with the tissue removal device via an aspiration line 3222. The tissue removal device may, for example, be the same or similar to the tissue removal device 3100 described above and illustrated in FIGS. 8 to 12. The tissue removal device 3100 may thus include the aspiration cannula 3104, and a linear actuator 3780 that drives the internal valve. In the present implementation, the linear actuator 3780 is pneumatically powered and thus receives pressurized gas from any suitable pressurized gas source 3702 via a gas line 3224. The aspiration cannula 3104 is schematically shown as being operatively inserted into a surgical site 3704 at which aspiration of tissue is desired, such as a patient's eye. A separate hand-held irrigation instrument 3706 is also shown as being operatively inserted into the surgical site 3704. An irrigation fluid source 3708 supplies the irrigation instrument 3706 with irrigation fluid via an irrigation fluid line 3710. The flow of irrigation fluid may be controlled by a valve 3712 or any other suitable means.

In the present implementation, the collection receptacle is positioned in-line between the tissue removal device 3100 and a vacuum source (e.g., a pump) 3714. The vacuum source 3714 may be any suitable device for generating vacuum such as, for example, the vacuum sources or pumps described earlier in the present disclosure. The collection receptacle includes at least one internal chamber for receiving aspirated tissue and fluid. The collection receptacle thus may include an inlet communicating with the aspiration line 3222 leading from the tissue removal device 3100, and an outlet communicating with a vacuum line leading to the vacuum source. At the outlet, the collection receptacle may include a filter or other device configured for separating liquid and solid material from gas, thereby ensuring that liquid and solid material do not flow through the vacuum line to the vacuum source 3714. A vacuum regulator 3730 is positioned in-line between the outlet of the collection receptacle and the vacuum source 3714. The vacuum regulator 3730 may be one or more components as needed to control the level of vacuum applied to the collection receptacle and/or tissue removal device 3100.

In the present implementation, the vacuum source 3714, or both the vacuum source 3714 and the pressurized gas source 3702, are integrated with a control console 3732. The control console 3732 may include other features as described above and illustrated in FIG. 1. A foot-operated control device may also be provided as described above and illustrated in FIG. 1. The control console 3732 may also include a valve control device 3784 configured for controlling the flow of pressurized gas from the pressurized gas source 3702 to the actuator 3780 of the tissue removal device 3100. The valve control device 3784 may have any suitable mechanical, electromechanical, or electromagnetic configuration for this purpose. The valve control device 3784 may communicate with vacuum pulse control circuitry and/or software of the control console 3732. Operating parameters of the valve control device 3784 (e.g., vacuum pulsing parameters) may be adjustable by the user via controls provided on the control console 3732 and/or the above-noted foot-operated control device. Also the present implementation, the collection receptacle is provided in the form of a cassette 3734 that is configured for removable installation by a user into a cassette receptacle 3736 (e.g., a hay, slot, etc.) of the console 3732. The console 3732 may include a device (not shown) for locking the cassette 3734 in place in the fully installed position (i.e., operative position), and for releasing the cassette 3734 from the installed position as desired by the user. The console 3732 may include a device (not shown) for providing an illuminated indication that the cassette 3734 has been installed in the installed position.

In the present implementation, the cassette 3734 includes a cassette housing 3738, a first (or primary) collection chamber 3740 in the cassette housing 3738, and a second (or secondary) collection chamber 3472 in the cassette housing 3738. The second collection chamber 3742 communicates with the first collection chamber 3740 via a cassette valve 3744 that may be a passive one-way valve or check valve. The cassette 3734 also includes an aspiration inlet 3746 communicating with the aspiration line 3222. For example, the aspiration inlet 3746 may include a fitting to which a tube of the aspiration line 3222 is coupled. The aspiration inlet 3746 communicates with the first collection chamber 3740. The cassette 3734 also includes a first vacuum port 3748 communicating with the first collection chamber 3740, and a second vacuum port 3750 communicating with the second collection chamber 3742. The first vacuum port 3748 and second vacuum port 3750 may communicate with the vacuum regulator 3730 via respective vacuum lines, and the vacuum regulator 3730 may communicate with the vacuum source 3714 via a common vacuum line. The cassette 3734 may also include one or more hydrophobic filters 3756 providing a liquid barrier between the first collection chamber 3740 and second collection chamber 3742 and the vacuum source 3714.

The vacuum regulator 3730 may be configured for controlling the respective vacuum levels in the first collection chamber 3740 and second collection chamber 3742. The cassette valve 3744 is configured such that it is closed when the pressure in the first collection chamber 3740 is lower than the pressure in the second collection chamber 3742 (i.e., when the vacuum level is higher in the first collection chamber 3740 than in the second collection chamber 3742), and is open when the pressure in the first collection chamber 3740 is higher than the pressure in the second collection chamber 3742 (i.e., when the vacuum level is lower in the first collection chamber 3740 than in the second collection chamber 3742). In a first tissue collection state (which may be a normal or initial tissue collection state), the first collection chamber 3740 may be utilized as the sole collection chamber, i.e., with the cassette valve 3744 closed. The first tissue collection state may be implemented by, for example, applying vacuum only to the first collection chamber 3740. In the first tissue collection state, the aspiration path runs from the aspiration cannula 3104, and through the aspiration line 3222 and aspiration inlet 3746, and into the first collection chamber 3740. The first collection chamber 3740 may be smaller (of lesser volume) than the second collection chamber 3742 to facilitate rapid adjustments to vacuum level. In a second tissue collection state (which may follow the first tissue collection state), both the first collection chamber 3740 and the second collection chamber 3742 may be utilized for tissue collection, i.e., with the cassette valve 3744 open. The second tissue collection state may be implemented by, for example, applying vacuum only to the second collection chamber 3742 or applying a higher level of vacuum to the second collection chamber 3742. In the second tissue collection state, the aspiration path thus additionally runs from the first collection chamber 3740, through the cassette valve 3744, and into the second collection chamber 3742. The second tissue collection state may be implemented when, for example, the amount of tissue and fluid being collected is great enough to warrant use of the larger second collection chamber 3742 to prevent the first collection chamber 3740 from completely filling up.

The cassette 3734 and/or the console 3732 may provide a fluid level indicator 3760 to monitor the level of aspirant (tissue and fluid) being accumulated in the first collection chamber 3740. The fluid level indicator 3760 may monitor one or more threshold levels and generate output signals to the console 3732 to initiate an appropriate response to the attainment of a particular threshold level. For instance, upon detecting one threshold level, the fluid level indicator 3760 may initiate a warning (audible, visual, etc.) to the user that the first collection chamber 3740 is approaching an overfill condition. Upon detecting a higher threshold level, the fluid level indicator 3760 may cause the vacuum regulator 3730 to switch from the first tissue collection state to the second tissue collection state, thereby opening the cassette valve 3744 and enabling aspirant to drain into the second collection chamber 3742. Upon detecting a yet higher threshold level, or detecting successive threshold levels at an undesirably short period of time (indicating that the first collection chamber 3740 is filling up too rapidly, the fluid level indicator 3760 may cause the vacuum regulator 3730 to divert application of vacuum away from the first and second vacuum ports 3748, 3750 and/or cause the vacuum source 3714 to be shut down. For such purposes, any suitable fluid level indicator may be provided. In the illustrated example, the fluid level indicator 3760 includes a floating ball 3762 that rises and falls with the level of aspirant in the first collection chamber 3740. The ball 3762 may be constrained to move substantially only in the direction of rising and falling aspirant by guide structures 3764 of the cassette housing 3738. One or more light sources 3766 (e.g., light emitting diodes, lasers, etc.) may be provided to direct one or more light beams through the first collection chamber 3740 to one or more light detectors 3768 photodiodes, photomultiplier tubes, etc.). Each light beam may correspond to a threshold level to be detected. As the surface of the aspirant rises, the ball 3762 moves into the path of a light beam, thereby breaking the light beam whereby attainment of the corresponding threshold level is detected. In a typical implementation, the light source(s) 3766 and light detector(s) 3768 are mounted in the console 3732, and are positioned so as to direct the light beam(s) at the correct elevation(s) through the first collection chamber 3740 when the cassette 3734 is installed in the console 3732.

In some implementations, the cassette 3734 (i.e., the cassette housing 3738) includes a fluid-routing chamber 3772 that is fluidly isolated from the first collection chamber 3740 and second collection chamber 3742. The fluid-routing chamber 3772 may be utilized, for example, to provide a coupling with the aspiration line 3222 (or with both the aspiration line 3222 and the gas line 3224), whereby the vacuum source 3714 (or both the vacuum source 3714 and the pressurized gas source 3702) are operatively coupled with the tissue removal device 3100 simply by installing the cassette 3734 in the console 3732. The fluid-routing chamber 3772 may also be utilized to provide permanent fluid couplings that cannot be disassembled by the user, thereby rendering the tissue removal device 3100 and the cassette 3734 a permanently assembled single unit, which single unit may be disposable by the user and replaced with a new or sterilized unit.

In the implementation specifically illustrated in FIG. 12, the fluid-routing chamber 3772 includes a cassette inlet 3774 through which the aspiration line 3222 and gas line 3224 pass from outside the cassette 3734. In this example, the aspiration inlet 3746 to which the aspiration line 3222 is coupled is located in the fluid-routing chamber 3772. Also in this example, the fluid-routing chamber 3772 includes a gas port 3776 leading to the outside of the cassette 3734. The gas line 3224 passes through the fluid-routing chamber 3772 and is coupled to the gas port 3776. The gas port 3776 may be located on the same side of the cassette 3734 as the first vacuum port 3748 and second vacuum port 3750. The console 3732 may include complementary respective couplings, such that upon installation of the cassette 3734, the gas line 3224 is automatically placed in communication with the pressurized gas source 3702, and the first collection chamber 3740 and second collection chamber 3742 are automatically placed in communication with the vacuum source 3714. The cassette 3734, particularly the cassette inlet 3774, may be configured such that the user cannot decouple the aspiration line 3222 and gas line 3224 from the cassette 3734. Moreover, the cassette 3734 may be configured such that the user cannot disassemble the cassette housing 3738 or access the cassette interior via the cassette inlet 3774, gas port 3776, first vacuum port 3748 or second vacuum port 3750.

Figure 13:
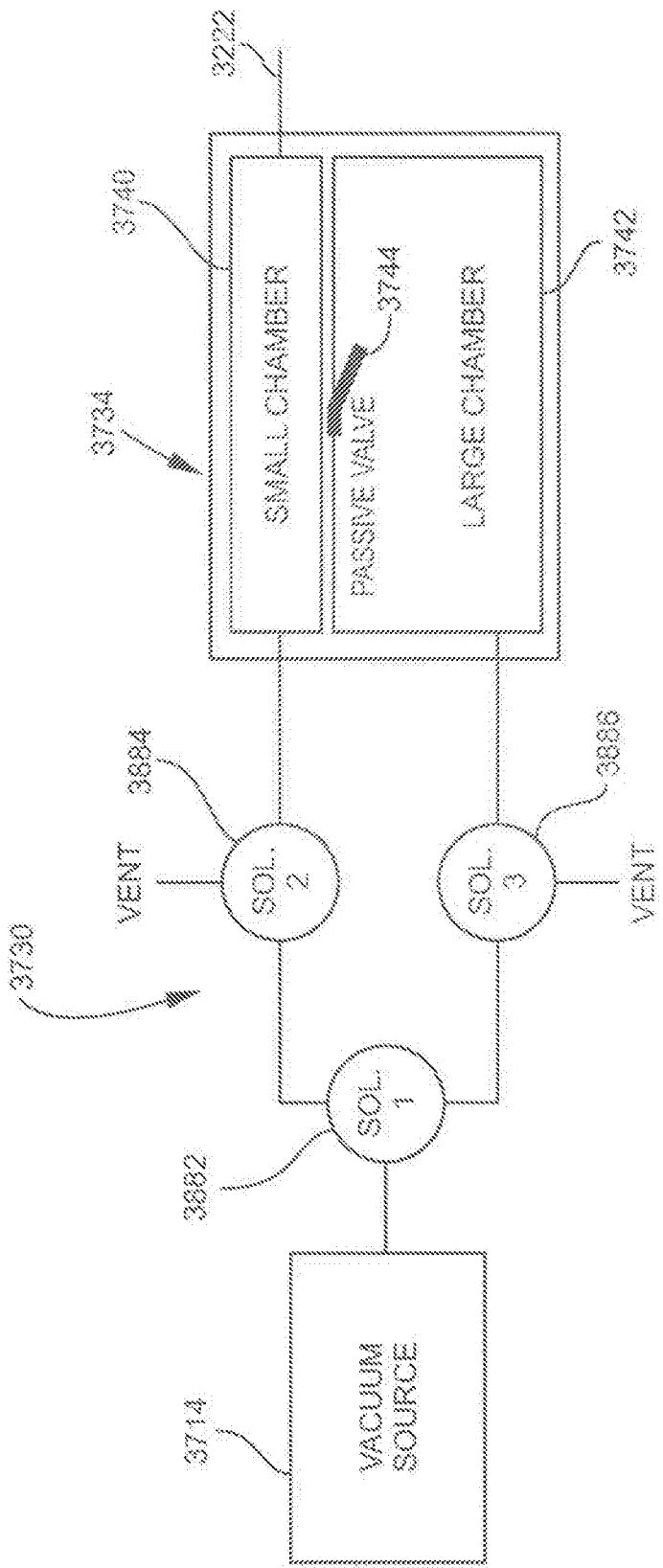
FIG. 13 is a schematic view of an example of a cassette, vacuum regulator and vacuum source that may be provided with the tissue removal system illustrated in FIG. 12.

FIG. 13 is a schematic view of an example of the cassette 3734, vacuum regulator 3730 and vacuum source 3714. In this implementation, the vacuum regulator 3730 includes a first valve 3882, a second valve 3884 and a third valve 3886. The first valve 3882 is in-line between the vacuum source 3714 and the second valve 3884 and third valve 3886, the second valve 3884 is in-line between the first valve 3882 and the first collection chamber 3740, and the third valve 3886 is inline between the first valve 3882 and the second collection chamber 3742. The valves 3882, 3884, 3886 may be of any suitable design, typically an active design, such as solenoid valves. In one example of a valve configuration, the valves 3882, 3884, 3886 are each movable to three positions. The first valve 3882 is movable to a closed position, an open position allowing vacuum to the second valve 3884, and an open position allowing vacuum to the third valve 3886. The second valve 3884 is movable to a closed position, an open position allowing vacuum to the first collection chamber 3740, and an open position leading to a vent. The third valve 3886 is movable to a closed position, an open position allowing vacuum to the second collection chamber 3742, and an open position leading to a vent. Hence, for example, the first tissue collection state (in which only the first collection chamber 3740 is utilized) may be implemented by opening the first valve 3882 to the second valve 3884, opening the second valve 3884 to the first collection chamber 3740, and closing the third valve 3886. The second tissue collection state (in which both the first collection chamber 3740 and second collection chamber 3742 are utilized) may be implemented by opening the first valve 3882 to the third valve 3886, opening the third valve 3886 to the second collection chamber 3742, and opening the second valve 3884 to vent.

It will be understood that other configurations of the valves 3882, 3884, 3886 are possible. For example, the first valve 3882 may be configured to have a position at which vacuum is open to both the second valve 3884 and third valve 3886 simultaneously. In this case, the second valve 3884 and third valve 3886 may be configured to have variable valve positions that enable the respective vacuum levels applied to the first collection chamber 3740 and second collection chamber 3742 to be independently adjusted.

FIGS. 14A and 14B are partially cut-away perspective and side views, respectively, of an example of the cassette 3734. The cassette housing 3738 includes an interior structure 3902 such as a wall that fluidly isolates the first collection chamber 3740 from the second collection chamber 3742. In this example, the cassette valve 3744 is a flapper valve that alternately opens and closes a bore 3904 formed through the interior structure 3902. The cassette housing 3738 also includes another interior structure 3906 such as a wall that fluidly isolates the fluid-routing chamber 3772 from the first collection chamber 3740. The aspiration inlet 3746 is mounted in communication with a fluid transfer passage 3908 that leads to the first collection chamber 3740. Inside the fluid-routing chamber 3772, the aspiration inlet 3746 and gas port 3776 are configured for coupling to tubing of the aspiration line 3222 and gas line 3224, respectively. The aspiration line 3222 and gas line 3224 pass through a feed-through member (or tube support member) 3910 that is securely mounted at the cassette inlet 3774. The feed-through member 3910 may serve as a strain relief for flexible tubing of the aspiration line 3222 and gas line 3224. In the illustrated example (similar to the feed-through member 3130 of the tissue removal device 3100 described above and illustrated in FIGS. 8 and 9), the feed-through member 3910 has a gap between two bores to accommodate a dual-lumen construction in which the aspiration line 3222 and gas line 3224 are integrally connected side-by-side. As described above, hydrophobic filters may be interposed between the first collection chamber 3740 and first vacuum port 3748 and between the second collection chamber 3742 and second vacuum port 3750. In the present implementation a single strip 3912 of hydrophobic filter material, mounted between the first vacuum port 3748 and second vacuum port 3750 on one side and the first collection chamber 3740 and second collection chamber 3742 on the other side, may be provided for this purpose.

Figure 15:
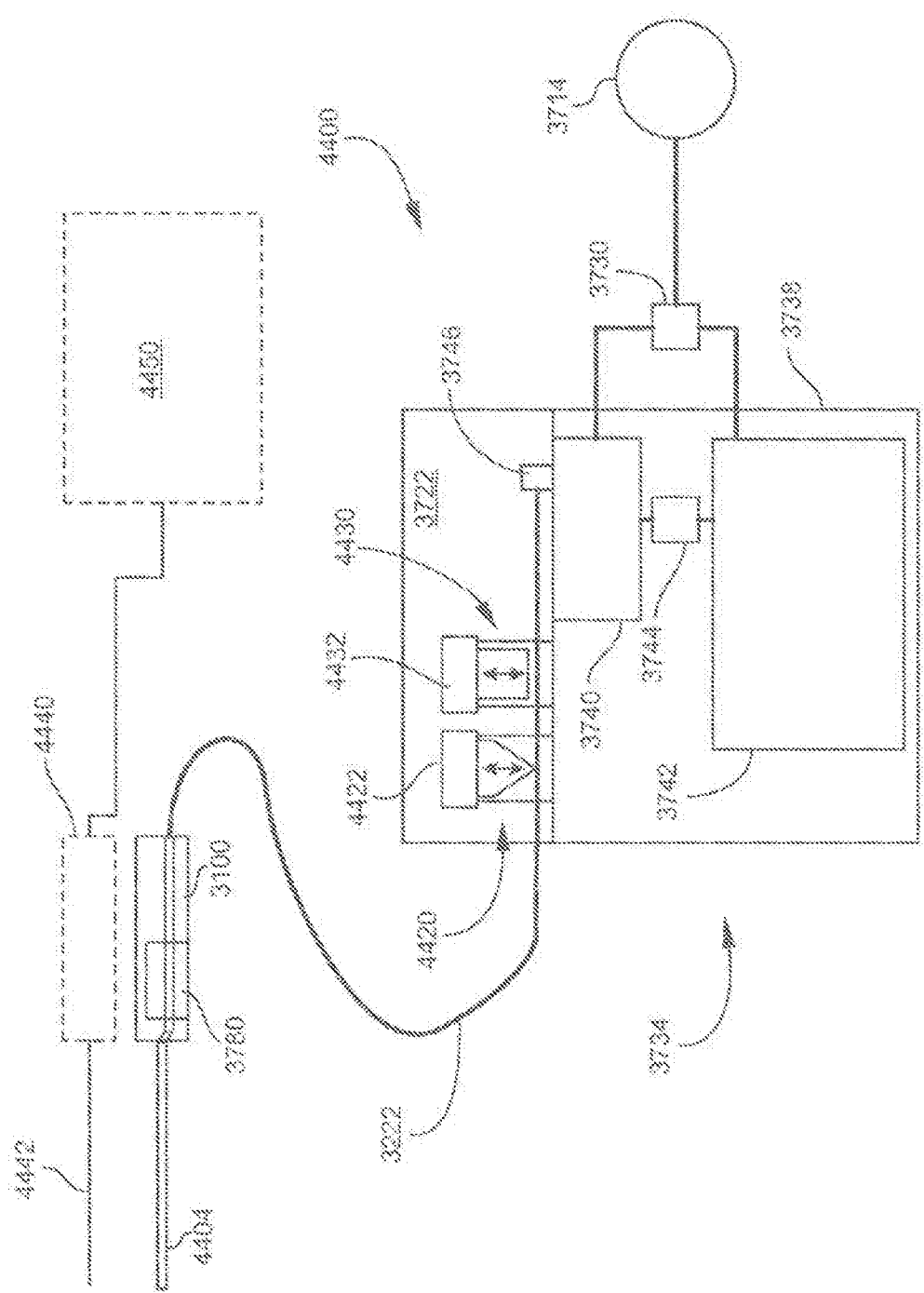
FIG. 15 is a schematic view of an example of a tissue removal system according to another implementation.

FIG. 15 is a schematic view of an example of a tissue removal system 4400 according to another implementation. The tissue removal system 4400 includes a tissue removal device and a tissue (and fluid) collection receptacle communicating with the tissue removal device via an aspiration line 3222. The tissue removal device may, for example, be the same or similar to the tissue removal device 3700 described above and illustrated in FIGS. 8 to 11B. The tissue removal device 4400 may thus include an aspiration cannula 4404, and a linear actuator 3780 that drives the internal valve. In the present implementation, the linear actuator 3780 is pneumatically powered as described with reference to FIG. 12. The operation of the pressurized gas source is not, however, illustrated in FIG. 15. A separate hand-held irrigation instrument is not shown in FIG. 15, but may be used as described with reference to FIG. 12.

In the example illustrated in FIG. 15, the collection receptacle is positioned in-line between the tissue removal device 3100 and a vacuum source (e.g., a pump) 3714. The vacuum source 3714 may be any suitable device for generating vacuum such as, for example, the vacuum sources or pumps described earlier in the present disclosure. The collection receptacle includes at least one internal chamber for receiving aspirated tissue and fluid. The collection receptacle may thus include an inlet communicating with the aspiration line 3222 leading from the tissue removal device 3100, and an outlet command siting with a vacuum line leading to the vacuum source. At the outlet, the collection receptacle may include a filter or other device configured for separating liquid and solid material from gas, thereby ensuring that liquid and solid material do not flow through the vacuum line to the vacuum source 3714. A vacuum regulator 3730 is positioned in-line between the outlet of the collection receptacle and the vacuum source 3714. The vacuum regulator 3730 may be one or more components as needed to control the level of vacuum applied to the collection receptacle and/or tissue removal device 3100.

In the present implementation, the tissue removal system includes a control console, which may operate as described above with reference to FIG. 12. The control console may include other features as described above and illustrated in FIG. 1. A foot-operated control device may also be provided as described above and illustrated in FIG. 1. The control console may also include a valve control device configured for controlling the flow of pressurized gas from the pressurized gas source 3702 to the actuator 3780 of the tissue removal device 3100 as describe above with reference to FIG. 12. The valve control device and other sensors, regulators, and electrical interfaces to controlled components may communicate with electronic circuitry and/or software of the control console 3732. A processor may be included in the control console to execute functions programmed in software. Functions performed under software control include adjustment of operating parameters of the valve control device (e.g., vacuum pulsing parameters), control of valves and regulators, and parameters that may be adjustable by the user via controls provided on the control console and/or the above-noted foot-operated control device.

In the present implementation, the collection receptacle is provided in the form of a cassette 3734 that is configured for removable installation by a user into a cassette receptacle 3736 (e.g., a bay, slot, etc.) of the console as shown in FIG. 12. The console may include a device (not shown) for locking the cassette 3734 in place in the fully installed position (i.e., operative position), and for releasing the cassette 3734 from the installed position as desired by the user. The console 3732 may include a device (not shown) for providing an illuminated indication that the cassette 3734 has been installed in the installed position.

In the present implementation as shown in FIG. 15, the cassette 3734 includes a cassette housing 3738, a first (or primary) collection chamber 3740 in the cassette housing 3738, and a second (or secondary) collection chamber 3472 in the cassette housing 3738. The second collection chamber 3742 communicates with the first collection chamber 3740 via a cassette valve 3744 that may be a passive one-way valve or check valve. The cassette 3734 also includes an aspiration inlet 3746 communicating with the aspiration line 3222. For example, the aspiration inlet 3746 may include a fitting to which a tube of the aspiration line 3222 is coupled. The aspiration inlet 3746 communicates with the first collection chamber 3740. The cassette 3734 also includes a first vacuum port communicating with the first collection chamber 3740, and a second vacuum port communicating with the second collection chamber 3742. The first and second vacuum ports may communicate with the vacuum regulator 3730 via respective vacuum lines, and the vacuum regulator 3730 may communicate with the vacuum source 3714 via a common vacuum line. Operation of the voltage regulator 3730 and control of the pressure between the first and second collection chambers 3740 and 3742 is described above with reference to FIG. 12.

In some implementations, the cassette 3734 (i.e., the cassette housing 3738) includes a fluid-routing chamber 3772 that is fluidly isolated from the first collection chamber 3740 and second collection chamber 3742. The fluid-routing chamber 3772 may be utilized, for example, to provide a coupling with the aspiration line 3222 (or with both the aspiration line 3222 and the gas line 3224), whereby the vacuum source 3714 (or both the vacuum source 3714 and the pressurized gas source 3702) are operatively coupled with the tissue removal device 3100 simply by installing the cassette 3734 in the console 3732. The fluid-routing chamber 3772 may also be utilized to provide permanent fluid couplings that cannot be disassembled by the user, thereby rendering the tissue removal device 3100 and the cassette 3734 a permanently assembled single unit, which single unit may be disposable by the user and replaced with a new or sterilized unit.

As shown in FIG. 15, a fluid circuit is formed by the aspiration cannula 4404, the valve-controlled cannula structure in the handpiece 3100, the aspiration line 3222, the first and second collection chambers 3740 and 3742, the vacuum regulator 3730, the vacuum source 3714, and the fluid connections between the first and second collection chambers 3740 and 3742 and the vacuum source 3714. A base vacuum is provided by the vacuum source 3714 in the fluid circuit. The vacuum is manipulated to aspirate in pulses by controlling the linear actuator 3780 to move the valve in the handpiece 3100. The handpiece 3100 may be similar to the handpiece described above with reference to FIG. 11B. For example, the valve port 3470 (in FIG. 11B) is alternately opened and closed by linear movement of the inner cannula 3338 (in FIG. 11B), which in the illustrated example not only serves as a valve component but also as part of the aspiration line through the handheld instrument. The axis of the aspiration cannula 4404 is offset from the axis of the inner cannula 3338 (in FIG. 11B), the aspiration cannula 4404 and the inner cannula 3338 (in FIG. 11B) may be parallel or substantially parallel, and the valve port 3470 (in FIG. 11B) is oriented transversely or substantially transversely to the aspiration cannula 4404 and the inner cannula 3338 (in FIG. 11B).

The opening and closing of the valve port 3470 (in FIG. 11B) may be controlled to manipulate the parameters of the vacuum pulses in order to produce desired effects. This is described further with reference to FIGS. 16A and 16B below.

The tissue removal system 4400 in FIG. 15 includes additional components not illustrated in FIG. 12. The system 4400 in FIG. 15 includes an aspiration cannula 4404 that is modified as described with reference to FIG. 45, although the system 4400 is not limited to using the specific aspiration cannula 4404 described below. The system 4400 in FIG. 15 includes a second valve 4420 and a third valve 4430 controlled by a first solenoid 4422 and a second solenoid 4432, respectively. The second valve 4420 may be implemented using an anvil tip positioned to contact the aspiration line 3222. The second valve 4420 may pinch the aspiration line 3222 shut when the first solenoid 4422 pushes the anvil tip into the aspiration line 3222. The first solenoid 4422 may be controlled to retract the anvil tip to re-open the aspiration line 3222. The third valve 4430 may be flat surface tip positioned to contact the aspiration line 3222. The third valve 4430 may be controlled by the second solenoid 4432 in the same way the first solenoid 4422 controls the second valve 4420.

The second valve 4420 and third valve 4430 are optional. Either the second valve 4420 or the third valve 4430 may be added to assist the first valve assembly 3110 (in FIG. 11B) in manipulating the vacuum in the fluid circuit. Either the second valve 4420 or the third valve 4430 may be added to purge the fluid circuit to clear tissue in the aspiration line 3222. Both the second valve 4420 and the third valve 4430 may be added to provide both valve manipulation and purging functions.

The system 4400 also includes an ultrasonic handpiece 4440 with an ultrasonic tip 4442 and a connection to a phacoemulsification system 4450. An option of the implementation of the system 4400 in FIG. 15 is to provide phacoemulsification to assist in breaking up the tissue. The ultrasonic tip 4442 may be implemented by insertion in a modified version of the aspiration cannula 4404 and by adding the ultrasonic functions of the ultrasonic handpiece 4440 to the handpiece 3100. The advantages of using a pulsed vacuum may be combined with the use of a phacoemulsification system to more effectively break up hard tissue such as hard cataracts. In addition to assisting in the breakup of the tissue, the pulsed vacuum may advantageously operate to keep the hard chunks of tissue near the tip more consistently thereby making the process more efficient.

Figure 16A:
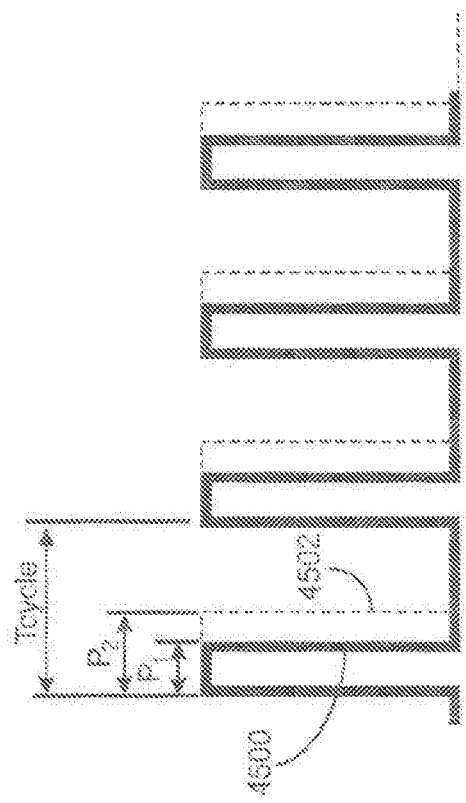
FIGS. 16A and 16B are pulsed vacuum signals illustrating control of pulse parameters to vary the pulsed vacuum.
Figure 16B:
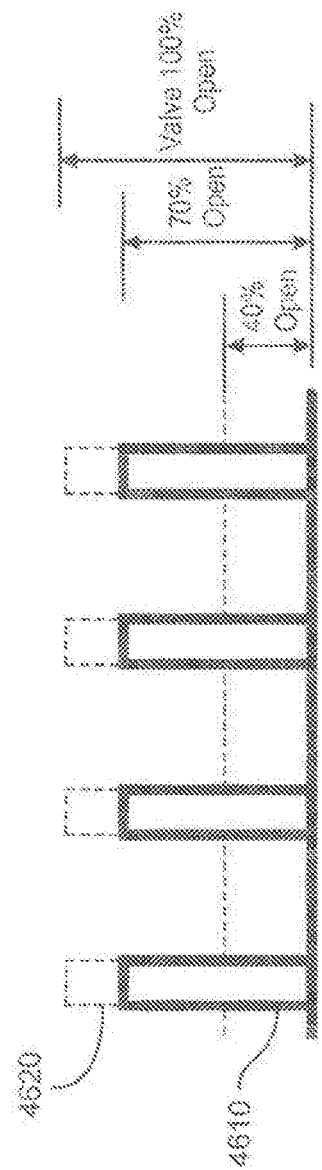

FIGS. 16A and 16B are pulsed vacuum signals illustrating control of pulse parameters to vary the pulsed vacuum. The control console 3732 (in FIG. 12), for example, may include a processor and programmed functions to control various vacuum pulse parameters using software. The software includes drivers or hardware interface functions to manipulate the vacuum source 3714, the linear actuator 3780, and other components to arrive at the vacuum pulse waveforms illustrated in FIGS. 16A and 16B. One vacuum pulse parameter is the frequency of any given stream of vacuum pulses. FIG. 16A shows a first vacuum pulse waveform 4600 and a second vacuum pulse waveform 4602 having the same period, $T_{cycle}$. The first vacuum pulse waveform 4600 and the second vacuum pulse waveform 4602 therefore have the same frequency=$1/T_{cycle}$. The processor may control the frequency of the vacuum pulses by controlling the total period, $T_{cycle}$, of each pulse and to drive the appropriate hardware components in accordance with a series of vacuum pulses of period $T_{cycle}$.

Another vacuum pulse parameter that may be controlled by the control console 3732 (in FIG. 12) is the duty cycle. The first pulse waveform 4600 in FIG. 16A shows that the vacuum is 'on' during a period of time $P_1$ and 'off' from $P_1$ to the end of the cycle, for a time $P_1$-$T_{cycle}$. The duty cycle of the first pulse waveform 4600 is the percentage of time $T_{cycle}$ during which the vacuum is 'on' The processor may control the duty cycle by adjusting the time during which the vacuum is 'on' without changing the frequency. The second pulse waveform 4602 shows the vacuum is 'on' during a period of time $P_2$ in the same total cycle time. $T_{cycle}$. The period of time $P_2$ is greater than the period of time $P_1$. Therefore the second pulse waveform 4602 has a longer duty cycle than the first pulse waveform 4600.

The processor may also adjust the extent to which the valve port 3470 (in FIG. 11B) is opened or closed to provide a throttle function for the vacuum. The vacuum pulses may thus be defined to be between a minimum vacuum level and a maximum vacuum level corresponding to a minimum valve open and a maximum valve open, respectively. If vacuum pulses alternate between the maximum vacuum level provided when the valve port 3470 is open 100%, and the minimum vacuum level when the valve port is when the valve port is open 0%, the hard pulse effect can create a vibration against the tissue, which can result in a pulsing of the entire anterior chamber. The processor may be programmed to control the opening of the valve port to be partially opened or partially closed at the maximum and minimum vacuum levels thus softening the impact of the pressure changes on the surrounding tissue.

FIG. 16B shows a first vacuum pulse waveform 4610 and a second vacuum pulse waveform 4620 having the same frequency and duty cycle. The first vacuum pulse waveform 4610 may be generated by controlling the valve port 3470 to close completely for a minimum vacuum level of 0, and open up to only 70% of the full opening area of the valve port 3470 for a maximum vacuum level of 70%. The second vacuum pulse waveform 4620 may be generated by controlling the valve port 3470 to close to 40% open for a minimum vacuum level of 40%, and open up to the full opening area of the valve port 3470 for a maximum vacuum level of 100%. Different effects may be achieved by defining other levels for the minimum and maximum vacuum levels.

The control console 3732 (in FIG. 12) may include a user interface that permits a user to define parameters or settings to fine tune control of the tissue removal system 4400 (in FIG. 15). For example, the control console 3732 may permit the user to define a flow rate (for example in cc/nm) by entering the setting into a user input device such as a touch screen or a keypad. The control console 3732 may provide software functions that determine the frequency, duty cycle, vacuum level, the base vacuum level and any other suitable and available parameter that would generate the vacuum pulses and provide the desired flow rate.

FIG. 17 is a schematic view of an example a tissue removal system 1700 according to another implementation. In this implementation, tissue removal may be performed by vacuum pulsing only, phacoemulsification only, both vacuum pulsing and phacoemulsification sequentially, or both vacuum pulsing and phacoemulsification simultaneously. The tissue removal system 1700 includes a tissue removal device 1800 and a tissue (and fluid) collection receptacle 1734 communicating with the tissue removal device 1800 via an external aspiration line 1722. One or more features or components of the tissue removal device 1800 may be the same or similar to those of the tissue removal device 3100 described above and illustrated in FIGS. 8 to 12. The tissue removal device 1800 may be configured for flowing irrigation fluid to the surgical site, or a separate hand-held irrigation instrument may be utilized as described above.

In the present implementation, the tissue removal device 1800 includes a hollow needle 1704 extending from the distal end of a housing (handpiece) 1740. The needle 1704 serves as both a phacoemulsification tip for breaking up tissue and as an aspiration cannula for removing broken up tissue from the surgical site. The tissue removal device 1800 includes an ultrasonic transducer 1714 configured for converting electrical energy to vibratory energy that propagates at a sonic or ultrasonic frequency. The ultrasonic transducer 1714 mechanically communicates with the needle 1704 so as to transfer the mechanical vibrations to the tip of the needle 1704, as appreciated by persons skilled in the art. As one non-limiting example, the ultrasonic transducer 1714 may include a piezoelectric element (or a stack of piezoelectric elements) coupled to the needle 1704 or to an intervening horn to which the needle 1704 is coupled such as by threading, as appreciated by persons skilled in the art. The needle 1704 is in fluid communication with an internal aspiration line 1744 that runs to a coupling member 1730 at the proximal end of the housing 1740. The coupling member 1730 may be any suitable fitting serving as an aspiration outlet of the tissue removal device 1800. One or more structures or components in the housing 1740 may in part define the internal aspiration line 1744 between the needle 1704 and the coupling member 1730.

The tissue removal system 1700 further includes a vacuum pulsing device 1716. Generally, the vacuum pulsing device 1716 is positioned in-line with the aspiration path between the needle 1704 and the tissue collection receptacle 1734, and is positioned external to the housing 1740 of the tissue removal device 1800 in a manner that isolates the vacuum pulsing device 1716 from the ultrasonic energy generated within the housing 1740. For example, damping material such as elastomeric sealing material may be interposed in one or more locations between the housing 1740 and the vacuum pulsing device 1716 to dampen vibrations. In the illustrated embodiment, the vacuum pulsing device 1716 is configured as an attachment to the housing 1740 (at the promixal end), in which case the vacuum pulsing device 1716 may be considered as being a part of the tissue removal device 1800. For example, the vacuum pulsing device 1716 may include a (second) coupling member 1738 configured for being coupled to the (first) coupling member 1730 of the tissue removal device 1800 in a fluid-tight manner. For example, one of the coupling members 1730 and 1738 may be a male fitting while the other is a female fitting. The vacuum pulsing device 1716 includes a valve assembly 1780 in a housing 1752. The valve assembly 1780 generally includes an actuator and a movable member or valve. The movable member is actuated by the actuator alternately between an open position and a closed position. The closed position obstructs or interrupts the vacuum established in the aspiration path. Hence, cycling the movable member between the open position and closed position generates vacuum pulses at the distal tip of the needle 1704, which is useful for breaking up tissue as described elsewhere in this disclosure.

Generally, the valve assembly 1780 may have any configuration suitable for generating vacuum pulses. Actuation may be done in a linear or rotary direction, and may be driven by pneumatics, mechanical means, electrical means, electromechanical means, magnetic means, or electromagnetic means. Examples of configurations for the valve assembly include, but are not limited to, those described above and illustrated in FIG. 1 (vacuum pulsing device 156), FIGS. 4A and 4B (vacuum pulsing device 1056), FIGS. 5A and 5B (vacuum pulsing device 1256), FIG. 6 (movable member 1406), FIGS. 7A and 7B (vacuum pulsing device 1556), and FIGS. 8 to 11B (valve assembly 3110 with offset, reciprocating inner cannula 3338, and outer cannula 3466 with valve port 3470, piston 3340, diaphragm 3454, etc.). A power line (electrical, pneumatic, etc.) is coupled to the actuator to provide power from a suitable power source. In the illustrated implementation, the valve assembly 1780 is pneumatically powered and thus receives pressurized gas from any suitable pressurized gas source 3702 via a gas line 1724 and a gas inlet 1754 of the vacuum pulsing device 1716.

In the present implementation, the tissue collection receptacle 1734 is positioned in-line between the tissue removal device 1800 and a vacuum source (e.g., a pump) 3714. Also in the present implementation, an external aspiration line 1722 is coupled to an aspiration outlet 1758 of the vacuum pulsing device 1716 and to the tissue collection receptacle 1734. Thus, the aspiration path generally runs from the needle 1704 and through the internal aspiration line 1744, the couplings 1730 and 1738, one or more internal conduits of the vacuum pulsing device 1716, the aspiration outlet 1758, and the external aspiration line 1722, and into the tissue collection receptacle 1734. The vacuum source 1714 may be any suitable device for generating vacuum such as, for example, the vacuum sources or pumps described earlier in the present disclosure. In some implementations, the tissue collection receptacle 1734 may be configured as a cassette as described above and illustrated in FIG. 12 (cassette 3734). A vacuum regulator 3730 may positioned in-line between the outlet of the tissue collection receptacle 1734 and the vacuum source 3714. The vacuum regulator 3730 may be one or more components as needed to control the level of vacuum applied to the tissue collection receptacle 1734 and/or tissue removal device 1800, as described above.

In the present implementation, the vacuum source 3714, or both the vacuum source 3714 and the pressurized gas source 3702, are integrated with a control console 1732. The control console 3732 may include other features as described above and illustrated in FIGS. 1 and 12. A foot-operated control device may also be provided as described above and illustrated in FIG. 1. The control console 1732 may also include a valve control device 3784 configured for controlling the flow of pressurized gas from the pressurized gas source 3702 to the actuator of the vacuum pulsing device 1716. The valve control device 3784 may have any suitable mechanical, electromechanical, or electromagnetic configuration for this purpose, as described above. The valve control device 3784 may communicate with vacuum pulse control circuitry and/or software of the control console 1732. Operating parameters of the valve control device 3784 (e.g., vacuum pulsing parameters) may be adjustable by the user via controls provided on the control console 1732 and/or the above-noted foot-operated control device. Also the present implementation, the tissue collection receptacle 1734 may be provided in the form of a cassette that is configured for removable installation by a user into a cassette receptacle 1736 (e.g., a bay, slot, etc.) of the console 1732, as described above.

In some implementations, the tissue collection receptacle 1734 may include a fluid-routing chamber such as described above in conjunction with FIG. 12 (fluid-routing chamber 3772) in which various lines (aspiration, gas, power, etc.) are installed in a permanent manner, as described above in conjunction with FIG. 12. By this configuration, the tissue collection receptacle 1734 and the vacuum pulsing device 1716, or the tissue collection receptacle 1734 and both the vacuum pulsing device 1716 and the tissue removal device 1800, may be provided as a permanently assembled single unit that cannot be disassembled by the user, and which single unit may be disposable by the user and replaced with a new or sterilized unit.

The tissue removal system 1700 further includes an electrical power source 1790 for supplying power to the ultrasonic transducer 1714 via a power line 1792. The power source 1790 may be included in the control console 1732 as schematically illustrated. The control console 1732 may also include a controller 1794 configured for controlling various components of the tissue removal system 1700. The controller 1794 may be an electronic processor-based controller and may include both hardware and software attributes, as appreciated by persons skilled in the art. The controller 1794 may be configured to control or perform, in whole or in part, any of the methods disclosed herein. In FIG. 17 the controller 1794 schematically shown to be in signal communication with the power source 1790, the valve control device 3784, and the vacuum source 3714 (and/or the vacuum regulator 3730). The controller 1794 may also be in signal communication with the slot that receives the tissue collection receptacle 1734 (in cassette-based embodiments), for example to determine that the tissue collection receptacle 1734 has been plugged into the control console 1732. The controller 1794 may also be in signal communication with a fluid level detector (as described above) if provided. The controller 1794 may thus be configured to control (set and adjust) the operating parameters of the ultrasonic transducer 1714 (ON/OFF, frequency, etc.), the vacuum pulsing device 1716 (ON/OFF, pulse magnitude, duration, frequency, duty cycle, etc., as shown for example in FIGS. 2, 3, 16A and 16B), and the vacuum source 3714 (ON/OFF, vacuum level, etc.).

The controller 1794 may be configured to switch the tissue removal system 1700 among any of the various operating modes disclosed herein. These operating modes include a phacoemulsification-only mode, a vacuum pulsing-only mode, and combined phacoemulsification-vacuum pulsing modes. In the phacoemulsification-only mode, the ultrasonic transducer 1714 is activated to excite the needle 1704 whereby the needle 1704 applies ultrasonic energy to the target tissue. In this mode, the vacuum source 3714 is activated to apply a desired level of vacuum to the needle 1704 to aspirate tissue broken up by the phacoemulsification modality. The aspiration path passes through the vacuum pulsing device 1716 but the vacuum pulsing device 1716 does not apply vacuum pulses. In the vacuum pulsing-only mode, the vacuum pulsing device 1716 is activated to apply vacuum pulses at the distal tip of the needle 1704 to break up tissue. In this mode, the vacuum source 3714 is activated to aspirate broken up tissue through the needle 1704 and vacuum pulsing device 1716, but the needle 1704 is not being vibrated. In combined phacoemulsification-vacuum pulsing modes, both the ultrasonic transducer 1714 and the vacuum pulsing device 1716 are active, either sequentially or simultaneously, or according to a multi-stage process entailing a sequence of one or more vacuum pulsing-only stages, phacoemulsification-only stages, and simultaneous phacoemulsification-vacuum pulsing stages. The surgeon may select different modes by inputting commands into the control console 1732, a foot-operated control device (foot pedals), or both.

Figure 18:
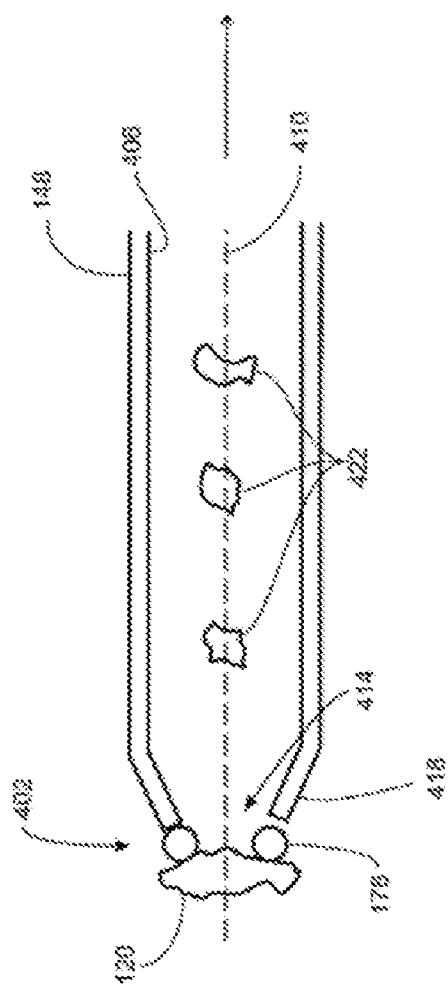
FIG. 18 is a cross-sectional view of an example of a thermal element and a cannula that may be provided by a tissue removal device according to an implementation disclosed herein.
Figure 19:
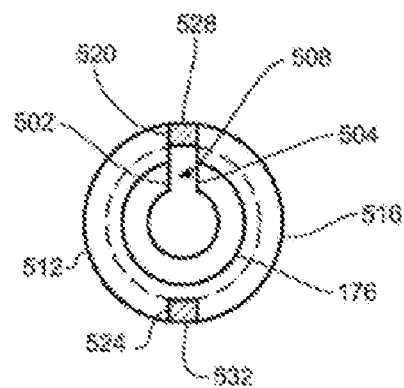
FIG. 19 is an end view of the thermal element and cannula from an outside perspective.

As described in U.S. Ser. No. 13/234,672 (the contents of which were incorporated by reference), FIG. 18 is a cross-sectional view of an example of a distal region of the tissue removal device 104. More specifically FIG. 18 illustrates, in cross-section, a distal region of the cannula 148 and the thermal element 176 positioned at a distal tip 402 of the cannula 148. An inner surface 406 of the cannula 148 circumscribes the interior of the cannula 148. The inside diameter of the inner surface 406 dictates the cross-sectional flow area through the cannula 148. In this example, the thermal element 176 and the cannula 148 are coaxially arranged about a longitudinal axis 410. An arrow collinear with the longitudinal axis 410 generally depicts the direction of the pressure gradient established by the applied vacuum and thus the direction of fluid flow and tissue aspiration. In this example, the thermal element 176 is provided in the form of a wire loop that defines an opening that serves as a fluid inlet 414 into the cannula 148 and thus corresponds to the open distal end 132 (FIG. 1) of the tissue removal device 104. Accordingly, the thermal element 176 is annular and coaxially surrounds the flow path for aspirated fluid and tissue. The size (internal diameter) of the fluid inlet 414 dictates the flow area into the cannula 176. This is also illustrated in FIG. 19, which is an end view of the thermal element 176 and cannula 148 from an outside perspective. The internal diameter of the thermal element 176 may be the same or substantially the same as the internal diameter of the cannula 148, in which case the flow area is preserved along the axial length of the cannula 148. In other implementations, as illustrated in FIGS. 18 and 19, the internal diameter of the thermal element 176 may be less than the internal diameter of the cannula 148, with the diametrical transition being provided by a tapered (or conical) section 418 of the cannula 148. This configuration may be useful for preventing the cannula 148 from clogging because any tissue small enough to traverse the fluid inlet 414 defined by the smaller-diameter thermal element 176 carries little risk of clogging the larger cross-sectional flow area defined by the cannula 148. As shown in FIG. 19, the thermal element 176 may be C-shaped in that it has two terminal ends 502, 504 separated by a gap 508. By this configuration, respective electrical leads may be attached or otherwise placed in electrical contact with the terminal ends 502, 504 to complete the circuit for passing DC current through the thermal element 176. The electrical leads may in turn communicate with the control console 112 via the heating signal line 180 diagrammatically depicted in FIG. 1.

The tissue removal device 104 may be utilized in a variety of procedures that entail inserting the cannula 148 into a surgical site via an incision. For instance, in various ophthalmological procedures, an incision may be made through a membrane of a patient's eye. The incision may be made by various techniques such as, for example, a laser procedure. To minimize damage to the eye and minimize post-surgery recovery and healing periods, the incision should be as small as possible. Therefore, the cannula 148 should be as small as practicably possible. The design of the cannula 148 and thermal element 176 disclosed herein enables the sizes of these components to be minimized without adversely affecting their functions. In some implementations, the outer diameter of the cannula 148 ranges from about 1.0-3.0 mm. In some examples, the outer diameter of the cannula 148 is about 3.0 mm, 2.5 mm, 2.0 mm, 1.5 mm, or LO mm. As noted elsewhere, the outer diameter of the thermal element 176 may be about the same or less than the outer diameter of the cannula 148. In some examples, the outer diameter of the thermal element 176 is about 1.7 mm or less. The size of the cannula 148 is able to be minimized in part because the tissue removal device 104 itself is not required to provide a means for supplying irrigation fluid to the surgical site. The utilization of the vacuum pulsing effect and the thermal effect disclosed herein does not require nearly as much irrigation fluid as tissue removal techniques of the prior art. Any irrigation fluid needed to be added to the surgical site may be supplied by a separate hand-held device. This may be referred to as a bimanual technique in which the surgeon wields the tissue removal device 104 in one hand and an irrigating device in the other hand as needed. Alternatively, the tissue removal device 104 may be configured for performing a coaxial technique in which irrigation fluid is supplied by the tissue removal device 104 through an annular sleeve (not shown) coaxial with the cannula 148. This latter alternative would require a larger incision, although the incision may still be less than 3.0 mm.

FIG. 18 also illustrates an example of the thermal effect implemented by the thermal element 176. In this example, the target tissue 120 (such as, for example, a cataract or portion of a cataract) has been drawn to the fluid inlet 414 under the influence of the applied vacuum. The target tissue 120, however, is larger than the fluid inlet 414 and hence initially comes into contact with the thermal element 176 and occludes the fluid inlet 414. In some situations, the applied vacuum may be sufficient to deform the target tissue 120 enough to enable the target tissue 120 to traverse through the fluid inlet 414 and flow through the cannula 148, out from the tissue removal device 104, and through associated aspiration lines to a desired destination (e.g., the collection site 128 illustrated in FIG. 1). In other situations, the target tissue 120 may be too large and/or not sufficiently deformable to be aspirated solely under the influence of the applied vacuum, and/or the implementation of the vacuum pulsing effect may not be effective enough to break up the target tissue 120. In these latter situations, the thermal element 176 may be energized to apply heat energy to the target tissue 120 and thereby break up the target tissue 120 into smaller fragments 422 more easily transported through the fluid inlet 414 and cannula 148.

Additionally, the tissue removal system 100 may be configured to detect the occurrence of occlusion and automatically activate the thermal element 176. Various approaches may be taken for detecting the occluding event. As one non-limiting example, the tissue removal system 100 may provide a pressure transducer 184 (FIG. 1), operatively interfaced with the aspiration line 152 at an appropriate location thereof, which provides continuous or intermittent pressure feedback signals to the control console 112 via a pressure feedback signal line 188. The detection of an abrupt change in pressure (or vacuum) level in the aspiration line 152 may be interpreted as the occurrence of an occluding event at the fluid inlet 414 (FIG. 4) and automatically trigger activation of the thermal element 176. Likewise, when the tissue removal system 100 is operating in continuous vacuum mode, the detection of an occluding event may trigger activation of the vacuum pulsing mode. The control console 112 may be configured to decide whether to automatically trigger the vacuum pulsing mode and/or the thermal application mode, and whether to activate both modes simultaneously or sequentially, depending on the current state of operation of the tissue removal device 104 at the time of detection of an occlusion. When it is subsequently detected that the occlusion has been lost, the control console 112 may be configured to deactivate the vacuum pulsing device 156 and/or the thermal element 176, and/or may shut down the vacuum pump(s) 108, 168 or otherwise cause vacuum to be cut off at the distal tip 402. For the purpose of detecting occlusions, the pressure transducer 184 may be positioned in the housing 140 (FIG. 1) of the tissue removal device 104 in operative communication with some portion of the internal aspiration line 144. Alternatively, as shown in FIG. 1 the pressure transducer 184 may be positioned in operative communication with the external aspiration line 152 or 164, or within the housing of the vacuum pump 108 or 168.

It will be noted that the effectiveness of the thermal effect does not in all situations require actual contact between the target tissue 120 and the thermal element 176. For instance, upon inserting the distal tip 402 of the cannula 148 into a surgical site, the thermal element 176 may be located at a small distance from the target tissue 120. The thermal element 176 may then be activated while it is in proximity to, but not contacting, the target tissue 120. Heat energy from the thermal element 176 may be transferred to the target tissue 120 through a small portion of the fluid medium existing between the thermal element 176 and the target tissue 120 such as air or fluid (e.g., intraocular fluid in the case of an ophthalmologic procedure, and/or irrigation fluid as may be applied in a variety of surgical procedures). A sufficient amount of heat energy may be transferred through the fluid medium to cause the target tissue 120 to begin to break up prior to the target tissue 120 being drawn to the fluid inlet 414 surrounded by of the thermal element 176. Alternatively or additionally, the target tissue 120 may begin to break up while in transit toward the fluid inlet 414 due to the transfer of heat from the thermal element 176.

In all such situations, it is evident that the thermal effect is highly localized. The thermal element 176 is shaped so as to present an outer surface area that concentrates the emitted heat energy directly into the fluid inlet 414 and the immediate vicinity of the fluid inlet 414. The thermal effect is effective and rapid enough that no substantial portion of fluid volume in which the target tissue 120 resides needs to become heated to any appreciable degree. The thermal effect is also effective and rapid enough that the heat energy need only be applied for a very brief period of time. This period of time is insufficient for surrounding non-targeted tissue to be adversely affected by the applied heat energy. This is particularly so in procedures entailing the circulation of irrigation fluid through the surgical site as the irrigation fluid absorbs excess heat energy deposited by the thermal element 176. The period of time for heat activation may also be minimized by applying pulses of heat energy as noted above, in procedures where a pulsed thermal effect is found to be more effective than a constant application of heat. Moreover, the thermal element 176 is positioned, sized and shaped such that the surgical site is exposed to a minimal surface area of the thermal element 176. As an example, the distance over which the thermal element 176 extends axially outward from the distal tip 402 of the cannula 148 may be about 2 mm or less. In other implementations, the thermal element 176 may be positioned so as to be partially or fully recessed within the distal tip 418 of the cannula 148.

Figure 20:
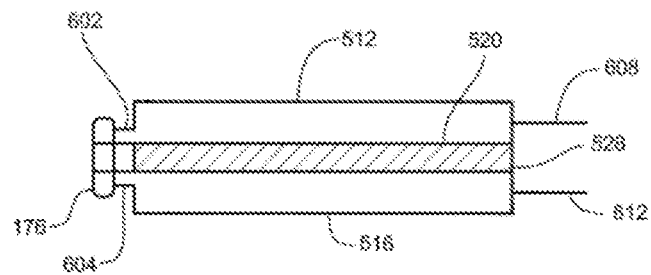
FIG. 20 is a top view of the thermal element and cannula illustrated in FIGS. 4 and 5.

FIGS. 18 and 19 additionally illustrate an implementation in which the structure of the cannula 148 itself is utilized to conduct DC current to the thermal element 176. This implementation is also illustrated in FIG. 20, which is a top view of the thermal element 176 and cannula 148 illustrated in FIGS. 18 and 19. In this case, the cannula 148 has a split-structured design in which the cannula 148 includes two C-shaped or semicircular, electrically conductive structural members 512, 516 extending along the longitudinal axis 410. The structural members 512, 516 may be composed of any suitable conductive material. In advantageous implementations, the structural members 512, 516 are composed of a material that is a very good conductor, i.e., conducts electricity very efficiently and thus without generating undue amounts of resistive heat. In this manner, the thermal effect imparted by the thermal element 176 remains localized at the distal tip 402 of the cannula 148 and very little heat is emitted by the cannula 148. This is particularly useful for avoiding thermal damage to membranes or other tissues through which an incision has been made and which may therefore be in direct contact with the outer perimeter of the cannula 148 extending through the incision. Non-limiting examples of materials suitable for the cannula members 512, 516 include aluminum, copper, nickel, and various precious metals (e.g., gold, silver, platinum, etc.).

From the perspective of FIG. 19, the structural members 512, 516 of the cannula 148 are separated from each other by an upper gap 520 and a diametrically opposing lower gap 524. As shown in FIG. 20, the gaps 520, 524 are axially elongated and continue along the entire axial distance of the cannula 148. By this configuration, the two members 512, 516 are electrically isolated from each other and hence may be utilized as electrical conduits for passing DC current to the thermal element 176. For this purpose, the two members 512, 516 may include respective extensions 602, 604 (or projections, tabs, or the like) in electrical contact with the terminal ends 502, 504 of the thermal element 176. All other conductive portions of the cannula 148 are physically separated from the thermal element 176. As diagrammatically depicted in FIG. 20, the two members 512, 516 may respectively communicate with two other electrical conductors 608, 612 that may be provided in the tissue removal device 104, which in turn may communicate with or form a part of the heating signal line 180 shown in FIG. 1.

To fully enclose the fluid volume circumscribed by the cannula 148 and seal this part of the aspiration line, axially elongated seals 528, 532 may be positioned so as to respectively fill the gaps 520, 524 between the cannula members 512, 516. The axial seals 528, 532 may be composed of any suitable electrically insulating material. In other implementations, the seals 528, 532 may be radial projections extending from a structure of the tissue removal device 104 external to the cannula 148, such as a cylinder that partially or fully surrounds the two members 512, 516 of the cannula 148. The seals 528, 532 may also extend from or be supported by an internal portion of the housing 140 of the tissue removal device 104.

Figure 21:
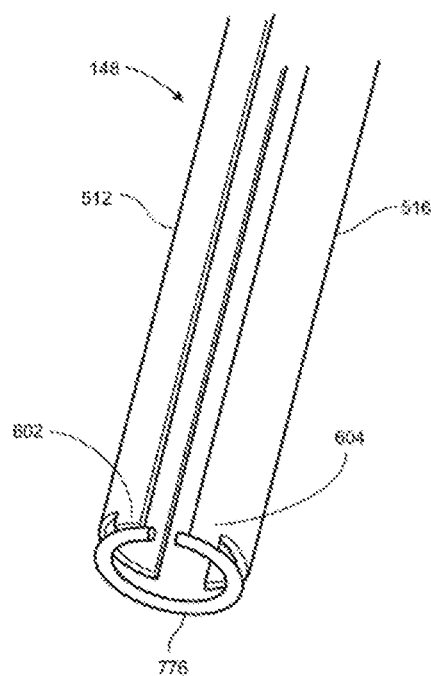
FIGS. 21, 22 and 23 are perspective views of the cannula and respective examples of how the thermal element may be structured.
Figure 22:
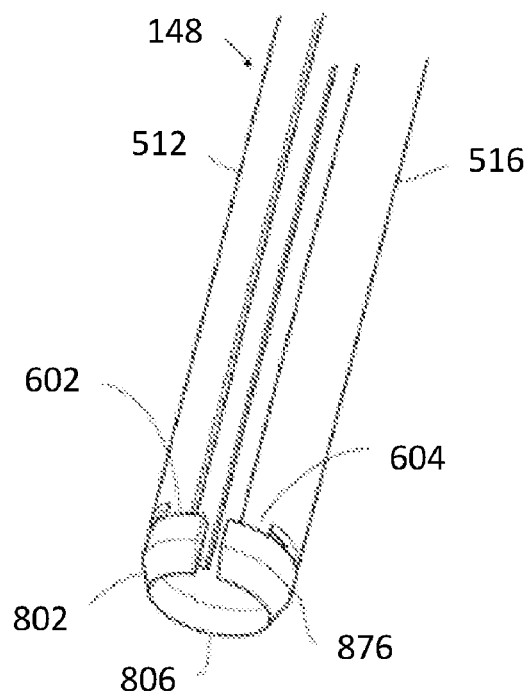
Figure 23:
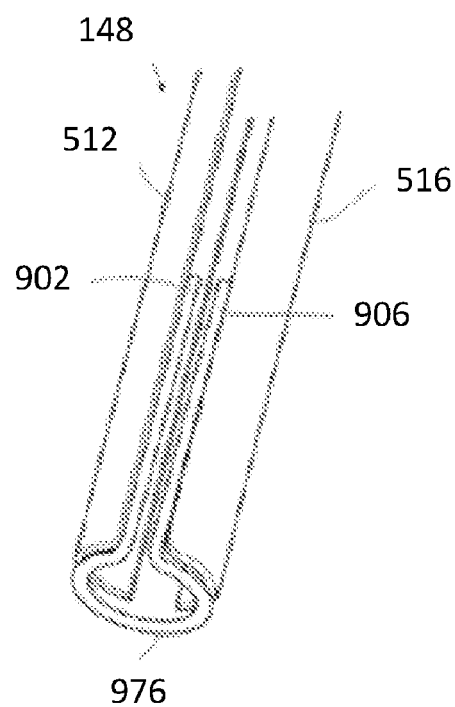

FIGS. 21, 22 and 23 are perspective views of the distal portion of the cannula 148 and respective examples of how the thermal element may be structured. In each of these examples, the cannula 148 has the above-described split design with two curved members 512, 516 electrically isolated from each other. For ease of illustration, seals interposed between the members 512, 516 are not shown. Also, in these examples, the cannula 148 has a constant diameter. FIG. 21 illustrates a thermal element 776 that is ring-shaped with a gap 508, similar to that described above and illustrated in FIGS. 18, 19 and 20. FIG. 22 illustrates a thermal element 876 that is also ring-shaped with a gap 508. In comparison to FIG. 21, the thermal element 876 of FIG. 22 has a larger axial dimension. This facilitates shaping the thermal element 876 for specific purposes. For instance, as shown in FIG. 22, a distal-most portion 802 of the thermal element 876 may taper down to a sharp edge 806, which may assist in breaking up large target tissue drawn into contact with the thermal element 876 and/or provide an even more localized thermal effect at the sharp edge 806. In addition, the inside diameter of distal-most portion 802 may taper down from the inside diameter of the cannula 148 to prevent clogging in a manner similar to the tapered section 418 of the cannula 148 illustrated in FIGS. 18, 19 and 20. FIG. 23 illustrates a thermal element 976 that includes two axial legs 902, 906 extending in the axial direction along at least a portion of the length of the cannula 148. The axial legs 902, 906 may, for example, be positioned in one of the gaps between the split members 512, 516 of the cannula 148. The axial legs 902, 906 may be provided to extend the thermal effect over a desired length of the distal region of the cannula 148.

The positions of the thermal elements 776, 876, 976 may be fixed relative to their respective cannulas 148 in any suitable manner. For example, in FIG. 21 the terminal ends of the thermal element 776 may be placed in electrical communication with the respective cannula extensions 602, 604 by welding, soldering, or an electrically conductive adhesive. In FIG. 22, the thermal element 876 may be attached to its cannula 148 in a similar manner. In FIG. 23, the axial legs 902, 906 (serving as terminal ends) of the thermal element 976 may be attached to respective inside edges of its cannula 148 in a similar manner. Alternatively in FIG. 9, the axial legs 902, 906 may be attached to respective insulated wires (not shown) that run along the cannula 148 and in communication with the heater signal line 180 (FIG. 1). In this latter case, the structural members 512, 516 of the cannula 148 are composed of an electrically insulating material instead of a conductive material.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

Further, terms such as "coupled to," and "configured for coupling to" and "secured to" (for example, a first component is "coupled to" or "is configured for coupling to" or is "secured to" a second component) are used herein to indicate a structural, functional, mechanical, electrical, signal, optical, magnetic, electromagnetic, ionic or fluidic relationship between two or more components or elements. As such, the fact that one component is said to be coupled with a second component is not intended to exclude the possibility that additional components may be present between, and/or operatively associated or engaged with, the first and second components.

Although the previous description only illustrates particular examples of various implementations, the invention is not limited to the foregoing illustrative examples. A person skilled in the art is aware that the invention as defined by the appended claims can be applied in various further implementations and modifications. In particular, a combination of the various features of the described implementations is possible, as far as these features are not in contradiction with each other. Accordingly, the foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A tissue removal device for removal of tissue from an eye during surgery, comprising:
    a hollow needle comprising an open distal tip;
    an aspiration line communicating with the hollow needle and configured for communicating with a vacuum source, wherein the hollow needle and the aspiration line define an aspiration path from the distal tip to the vacuum source;
    a vacuum device configured for controlling a vacuum at the distal tip;
    a first collection chamber connected to the aspiration line;
    a second collection chamber a valve connected between the first collection chamber and the second collection chamber;
    a vacuum regulator configured to control vacuum levels in the first collection chamber and the second collection chamber applied by the vacuum device, wherein the vacuum regulator applies vacuum only to the first collection chamber in a first tissue collection state for tissue collection only in the first collection chamber, and wherein the vacuum regular applies vacuum to both the first and second collection chambers in a second tissue collection states for tissue collection in both the first and second collection chambers; and
    a restrictor at the distal tip of the hollow needle, the restrictor having an inner diameter smaller than an inner diameter of the hollow needle.

2. The device of claim 1, wherein the vacuum device comprises a vacuum pulsing device configured to provide vacuum pulses at an open end of the distal tip.

3. The device of claim 2, wherein the vacuum pulsing device comprises an actuator and a movable member, wherein the actuator is configured for moving the movable member alternately between a closed position that obstructs the aspiration path and an open position.

4. The tissue removal device of claim 3, wherein the actuator is pneumatically driven, mechanically driven, electrically driven, electromechanically driven, magnetically driven, or electromagnetically driven, and at least one of a vacuum pulse duration, a vacuum level, and a vacuum pulse frequency is set by operator control.

5. The tissue removal device of claim 3, wherein the actuator is configured for communicating with a valve control device such that the movable member is movable between the open position and the closed position to induce the vacuum pulses in an aspiration cannula of the vacuum pulsing device according to a controllable pulse parameter.

6. The tissue removal device of claim 2, wherein the vacuum pulsing device comprises a valve port through which the aspiration path passes, at an open position the valve port is open such that a vacuum applied at the distal tip, and at a closed position the valve port is closed such that the vacuum is prevent from being applied at the distal tip, and the valve port is configured to be adjustable between either totally closed or partially closed.

7. The tissue removal device of claim 6, wherein a movable member comprises an inner cannula, the vacuum pulsing device comprises an outer cannula coaxially disposed about at least a portion of the inner cannula, the valve port is formed in the outer cannula, at the open position the aspiration path passes from the valve port into the inner cannula, at the closed position the inner cannula blocks the valve port.

8. The tissue removal device of claim 7, wherein the vacuum pulsing device comprises an aspiration inlet communicating with the aspiration line in the housing, and a transition communicating with the aspiration inlet and adjoining the outer cannula at the valve port in a fluid-sealed manner, wherein the aspiration inlet extends along a first axis to the transition and the inner cannula extends along a second axis offset from the first axis.

9. The tissue removal device of claim 1, further comprising an ultrasonic transducer configured to provide phacoemulsification to assist in breaking up the tissue.

10. The tissue removal device of claim 1, wherein the restrictor comprises a ring-shaped component connected to the distal tip.

11. The tissue removal device of claim 10, further comprising a bypass of the ring-shaped component.

12. The tissue removal device of claim 1, further comprising a bypass of the tapered end component.

13. The tissue removal device of claim 1, wherein the restrictor comprises a thermal element for heating an obstruction occluding an opening at the distal tip.

14. The device of claim 1, further comprising a cassette for tissue collection, wherein at an installed position of the cassette in a cassette housing, the cassette communicates with the vacuum source, and the aspiration path runs through the cassette housing.

15. The device of claim 1, wherein the cassette comprises the first collection chamber connected to the aspiration line and the second collection chamber, and a cassette valve connected between the first collection chamber and the second collection chamber.

16. The device of claim 15, wherein
in operation, opening the cassette valve transfers broken-up tissue from the first collection chamber to the second collection chamber.

17. The tissue removal device of claim 1, comprising a control console configured for receiving user input to determine a flow rate in the aspiration path, and controlling the flow rate based on the user input by controlling a base vacuum provided by the vacuum source.

18. The tissue removal device of claim 17, wherein the control console is further configured for providing a pulsed vacuum as a series of the vacuum pulses having a vacuum on period followed by a vacuum off period to form a pulse period, the vacuum pulses being generated at a frequency determined by the pulse period.

* * * * *